(12) United States Patent
Minagawa et al.

(10) Patent No.: US 8,940,496 B2
(45) Date of Patent: Jan. 27, 2015

(54) **METHOD FOR DETECTING MICROORGANISMS BELONGING TO *MYCOPLASMA PNEUMONIAE* AND/OR *MYCOPLASMA GENITALIUM***

(75) Inventors: Atsuko Minagawa, Tokyo (JP); Toyomasa Hiroshima, Tokyo (JP); Yasushi Shimada, Tokyo (JP); Kazuyuki Sugiyama, Tokyo (JP); Yuki Mitobe, Tokyo (JP); Hatsue Itagaki, Tokyo (JP)

(73) Assignee: LSI Medience Corporation, Tokyo (JP)

( * ) Notice: Subject to any disclaimer, the term of this patent is extended or adjusted under 35 U.S.C. 154(b) by 56 days.

(21) Appl. No.: 13/513,557

(22) PCT Filed: Dec. 3, 2010

(86) PCT No.: PCT/JP2010/071652
§ 371 (c)(1),
(2), (4) Date: Jun. 1, 2012

(87) PCT Pub. No.: WO2011/068189
PCT Pub. Date: Jun. 9, 2011

(65) Prior Publication Data
US 2012/0244544 A1  Sep. 27, 2012

(30) Foreign Application Priority Data

Dec. 4, 2009 (JP) ............................... 2009-276115
Feb. 4, 2010 (JP) ............................... 2010-023102

(51) Int. Cl.
*G01N 33/569* (2006.01)
*C07K 16/12* (2006.01)
*C12Q 1/68* (2006.01)

(52) U.S. Cl.
CPC ............ *C07K 16/1253* (2013.01); *C12Q 1/689* (2013.01); *G01N 33/56933* (2013.01); *C12Q 2521/301* (2013.01); *G01N 2469/10* (2013.01)
USPC ....................................... 435/7.32; 530/389.5

(58) Field of Classification Search
CPC .......................... C07K 16/00; C07K 16/1253
See application file for complete search history.

(56) References Cited

U.S. PATENT DOCUMENTS

| 5,158,870 | A  | 10/1992 | Baseman et al. |
| 5,641,638 | A  | 6/1997  | Bredt et al. |
| 6,537,773 | B1 | 3/2003  | Fraser et al. |
| 2004/0014943 | A1 | 1/2004 | Matsuyama et al. |

FOREIGN PATENT DOCUMENTS

| EP | 0254384 A2 | 1/1988 |
| EP | 1245677 A1 | 10/2002 |
| JP | 63-000298 A | 1/1988 |
| JP | 05-304990 | 11/1993 |
| JP | 2002-306169 | 10/2002 |
| JP | 2004-73185 A | 3/2004 |
| WO | WO 01/57199 A1 | 8/2001 |

OTHER PUBLICATIONS

Musatovova et al. Transcriptional heat shock response in the smallest known self-replicating cell, *Mycoplasma genitalium*. J. Bacteriology (2006) vol. 188, No. 8, pp. 2845-2855.*
Kannan et al. Characterization of a unique ClpB protein of *Mycoplasma pneumoniae* and its impact on growth. Infection and Immunity (2008) vol. 76, No. 11, pp. 5082-5092.*
Dascher, C. et al; Heat Shock Response in Mycoplasmas, Genome-Limited Organisms; Journ. Of Bacteriology; 1990; vol. 172, No. 4; p. 1823-1827.
International Search Report for WO 2011/068189 A1.
Weiner et al., "Transcription profiles of the bacterium *Mycoplasma pneumoniae* grown at different temperatures," *Nucleic Acid Research* 31(21):6306-6320 (2003).
Su et al., "Mapping phosphoproteins in *Mycoplasma genitalium* and *Mycoplasma pneumonia*," *BMC Microbiology* 7:63 (2007).
Supplementary EP Search Report dated May 14, 2013 corresponding to EP 10834639.
GenBank L43967.2, *Mycoplasma genitalium* G37, complete genome, 2 pages, 2009.
Li et al., "Cloning and partial expression of the chaperones protein DnaK a Chinese strain of *Mycoplasma hyopneumoniae*," Chinese Journal of Preventive Veterinary Medicine, Mar. 2008, vol. 30, No. 3, pp. 169-173.
Qiao et al., "Preparation and identification of monoclonal antibodies against HSP70 of *Mycoplasma hyopneumoniae*," Chinese Veterinary Science, 2008(08): 701-706.
Accession NP_110122; Molecular chaperone DnaK [*Mycoplasma pneumoniae* M129], Jun. 2009, 1 page.

* cited by examiner

*Primary Examiner* — Kenneth R. Horlick
*Assistant Examiner* — David Thomas
(74) *Attorney, Agent, or Firm* — Kilpatrick Townsend & Stockton LLP

(57) ABSTRACT

A detection method and a detection kit for rapidly and specifically diagnosing *Mycoplasma pneumoniae* and/or *Mycoplasma genitalium* infections are provided. The DnaK of *Mycoplasma pneumoniae* or *Mycoplasma genitalium* is used as an indicator.

2 Claims, 10 Drawing Sheets

Figure 1

| M129_DnaK | ATGAGTACAGATAACGGCTTAATTATCGGCATTGACCTTGGTACCACTAACTCCTGTGTG | 60 |
| FH_DnaK | ATGAGTACAGATAACGGCTTAATTATCGGCATTGACCTTGGTACCACTAACTCCTGTGTG | 60 |
| | ************************************************************ | |
| M129_DnaK | TCGGTCATGGAGAATGGACGCCCAGTAGTGTTGGAAAACCCTGAAGGTAAACGCACCACC | 120 |
| FH_DnaK | TCGGTCATGGAGAATGGACGCCCAGTAGTGTTGGAAAACCCTGAAGGTAAACGCACCACC | 120 |
| | ************************************************************ | |
| M129_DnaK | CCTTCGATTGTTTCTTACAAGAACAACGAAATTATTGTGGGTGATGCTGCGAAACGGCAA | 180 |
| FH_DnaK | CCTTCGATTGTTTCTTACAAGAACAACGAAATTATTGTGGGTGATGCTGCGAAACGGCAA | 180 |
| | ************************************************************ | |
| M129_DnaK | ATGGTAACTAACCCTAATACTATTGTTTCCATTAAGCGTTTAATGGGTACCTCCAATAAG | 240 |
| FH_DnaK | ATGGTAACTAACCCTAATACTATTGTTTCCATTAAGCGTTTAATGGGTACCTCCAATAAG | 240 |
| | ************************************************************ | |
| M129_DnaK | GTAACCGTTAAGAATCCTGATGGTTCTACCAAAGAGTTAACTCCTGAAGAGGTATCAGCG | 300 |
| FH_DnaK | GTAACCGTTAAGAATCCTGATGGTTCTACCAAAGAGTTAACTCCTGAAGAGGTATCAGCG | 300 |
| | ************************************************************ | |
| M129_DnaK | CAAATCTTGAGCTACCTCAAGGACTATGCGGAAAAGAAGATTGGTAAAACGATTTCCCGT | 360 |
| FH_DnaK | CAAATCTTGAGCTACCTCAAGGACTATGCGGAAAAGAAGATTGGTAAAACGATTTCCCGT | 360 |
| | ************************************************************ | |
| M129_DnaK | GCTGTTATTACCGTACCTGCTTACTTTAACGATGCAGAACGGAACGCTACTAAAACCGCT | 420 |
| FH_DnaK | GCTGTTATTACCGTACCTGCTTACTTTAACGATGCAGAACGGAACGCTACTAAAACCGCT | 420 |
| | ************************************************************ | |
| M129_DnaK | GGTAAGATTGCTGGTTTAAACGTTGAGCGGATTATTAACGAACCTACCGCCGCTGCATTG | 480 |
| FH_DnaK | GGTAAGATTGCTGGTTTAAACGTTGAGCGGATTATTAACGAACCTACCGCCGCTGCATTG | 480 |
| | ************************************************************ | |
| M129_DnaK | GCTTATGGGATCGACAAGTCTAACCGAGAAATGAAAGTCTTGGTGTACGACCTTGGTGGT | 540 |
| FH_DnaK | GCTTATGGGATCGACAAGTCTAACCGAGAAATGAAAGTCTTGGTGTACGACCTTGGTGGT | 540 |
| | ************************************************************ | |
| M129_DnaK | GGTACCTTTGACGTTTCCTTACTTGACATTGCTGAAGGTACCTTCGAAGTATTAGCCACT | 600 |
| FH_DnaK | GGTACCTTTGACGTTTCCTTACTTGACATTGCTGAAGGTACCTTCGAAGTATTAGCCACT | 600 |
| | ************************************************************ | |
| M129_DnaK | GCTGGGGACAACCGTTTGGGTGGTGATGACTGGGACAACAAGATTATTGAGTTCATCTTA | 660 |
| FH_DnaK | GCTGGGGACAACCGTTTGGGTGGTGATGACTGGGACAACAAGATTATTGAGTTCATCTTA | 660 |
| | ************************************************************ | |
| M129_DnaK | GCGCACATTGCCCAAGAACACAATGGGCTTAACTTGTCCAATGACAAGATGGCTATGCAA | 720 |
| FH_DnaK | GCGCACATTGCCCAAGAACACAATGGGCTTAACTTGTCCAATGACAAGATGGCTATGCAA | 720 |
| | ************************************************************ | |

Figure 2

| M129_DnaK | CGCTTAAAGGAAGCGGCTGAACGTGCTAAGATTGAACTTTCCGCCCAACTAGAAGCAATT | 780 |
| FH_DnaK   | CGCTTAAAGGAAGCGGCTGAACGTGCTAAGATTGAACTTTCCGCCCAACTAGAAGCAATT | 780 |
|           | ************************************************************ |     |
| M129_DnaK | ATCTCTTTACCGTTCTTAACGGTTACCGAAAAGGGTCCGGTAAACGTTGAACTTAAGCTA | 840 |
| FH_DnaK   | ATCTCTTTACCGTTCTTAACGGTTACCGAAAAGGGTCCGGTAAACGTTGAACTTAAGCTA | 840 |
|           | ************************************************************ |     |
| M129_DnaK | ACCCGTGCTAAGTTTGAAGAAATTACCAAACAATTACTAGAACGTACTCGCAACCCAATT | 900 |
| FH_DnaK   | ACCCGTGCTAAGTTTGAAGAAATTACCAAACAATTACTAGAACGTACTCGCAACCCAATT | 900 |
|           | ************************************************************ |     |
| M129_DnaK | TCGGATGTTTTACGTGAAGCCAAGATTAAACCAGAAGAAATTAATGAAATCTTGTTGGTG | 960 |
| FH_DnaK   | TCGGATGTTTTACGTGAAGCCAAGATTAAACCAGAAGAAATTAATGAAATCTTGTTGGTG | 960 |
|           | ************************************************************ |     |
| M129_DnaK | GGTGGATCGACCCGGATGCCAGCAGTGCAAAAACTAGTGGAATCAATGGTACCAGGACAC | 1020 |
| FH_DnaK   | GGTGGATCGACCCGGATGCCAGCAGTGCAAAAACTAGTGGAATCAATGGTACCAGGACAC | 1020 |
|           | ************************************************************ |      |
| M129_DnaK | AGTCCAAACCGCTCAATTAACCCGGATGAGGTGGTAGCCATTGGTGCTGCCATCCAAGGG | 1080 |
| FH_DnaK   | AGTCCAAACCGCTCAATTAACCCGGATGAGGTGGTAGCCATTGGTGCTGCCATCCAAGGG | 1080 |
|           | ************************************************************ |      |
| M129_DnaK | GGTGTGTTACGCGGTGATGTAAAGGACGTGTTACTGTTGGACGTTACTCCTTTAACGCTC | 1140 |
| FH_DnaK   | GGTGTGTTACGCGGTGATGTAAAGGACGTGTTACTGTTGGACGTTACTCCTTTAACGCTC | 1140 |
|           | ************************************************************ |      |
| M129_DnaK | TCGATTGAAACCCTTGGTGGTGTAGCAACTCCGTTAATTAAGCGTAACACCACCATTCCT | 1200 |
| FH_DnaK   | TCGATTGAAACCCTTGGTGGTGTAGCAACTCCGTTAATTAAGCGTAACACCACCATTCCT | 1200 |
|           | ************************************************************ |      |
| M129_DnaK | GTAAGTAAGAGTCAAATCTTCTCTACAGCGCAAGACAACCAAGAATCAGTGGATGTGGTG | 1260 |
| FH_DnaK   | GTAAGTAAGAGTCAAATCTTCTCTACAGCGCAAGACAACCAAGAATCAGTGGATGTGGTG | 1260 |
|           | ************************************************************ |      |
| M129_DnaK | GTTTGTCAAGGGGAACGCCCAATGGCACGTGACAACAAGTCTTTGGGTCGCTTTAACTTA | 1320 |
| FH_DnaK   | GTTTGTCAAGGGGAACGCCCAATGGCACGTGACAACAAGTCTTTGGGTCGCTTTAACTTA | 1320 |
|           | ************************************************************ |      |
| M129_DnaK | GGGGGCATCCAACCAGCACCCAAGGGTAAACCCCAAATTGAAATTACCTTTAGCTTGGAC | 1380 |
| FH_DnaK   | GGGGGCATCCAACCAGCACCCAAGGGTAAACCCCAAATTGAAATTACCTTTAGCTTGGAC | 1380 |
|           | ************************************************************ |      |
| M129_DnaK | GCCAACGGGATCTTAAACGTGAAGGCTAAAGATTTAACCACTCAAAAGGAAAACAGTATT | 1440 |
| FH_DnaK   | GCCAACGGGATCTTAAACGTGAAGGCTAAAGATTTAACCACTCAAAAGGAAAACAGTATT | 1440 |
|           | ************************************************************ |      |

Figure 3

| M129_DnaK | ACTATTAGTGACAACGGCAACTTGTCCGAAGAGGAAATCCAAAAGATGATTCGTGATGCG | 1500 |
| FH_DnaK | ACTATTAGTGACAACGGCAACTTGTCCGAAGAGGAAATCCAAAAGATGATTCGTGATGCG | 1500 |
| | ************************************************************ | |
| M129_DnaK | GAAGCCAACAAGGAGCGTGACAATGTGATTCGTGAACGCATTGAGCTCCGTAACGAAGGT | 1560 |
| FH_DnaK | GAAGCCAACAAGGAGCGTGACAATGTGATTCGTGAACGCATTGAGCTCCGTAACGAAGGT | 1560 |
| | ************************************************************ | |
| M129_DnaK | GAAAGCATCGTGAGCACGATTAAGGAGATTCTCCAAAGTCCCGAAGCGAAGGACTTCCCT | 1620 |
| FH_DnaK | GAAAGCATCGTGAGCACGATTAAGGAGATTCTCCAAAGTCCCGAAGCGAAGGACTTCCCT | 1620 |
| | ************************************************************ | |
| M129_DnaK | AAAGAAGAGAAGGAAAAAACTCGACAAGATTACCGGTGGTATTGATGCAGCAATTAAGGCC | 1680 |
| FH_DnaK | AAAGAAGAGAAGGAAAAAACTCGACAAGATTACCGGTGGTATTGATGCAGCAATTAAGGCC | 1680 |
| | ************************************************************ | |
| M129_DnaK | AATGACTACACCAAGTTAAAAGCCGAAATCGAAAACTTCAAGAAGTGAAGGGAAGAAATG | 1740 |
| FH_DnaK | AATGACTACACCAAGTTAAAAGCCGAAATCGAAAACTTCAAGAAGTGAAGGGAAGAAATG | 1740 |
| | ************************************************************ | |
| M129_DnaK | GCCAAGAAGTACAACCCTAACGGGGATCAAGGTCAACCAGCACAATAA | 1788 |
| FH_DnaK | GCCAAGAAGTACAACCCTAACGGGGATCAAGGTCAACCAGCACAATAA | 1788 |
| | ************************************************ | |

Figure 4

| M129_P1 | ATGCACCAAACCAAAAAAACTGCCTTGTCCAAGTCCACTTGGATTCTCATCCTCACCGCC | 60 |
| FH_P1 | ATGCACCAAACCAAAAAAACTGCCTTGTCCAAGTCCACTTGGATTCTCATCCTCACCGCC | 60 |
|  | ************************************************************ |  |
| M129_P1 | ACCGCCTCCCTCGCGACGGGACTCACCGTAGTGGGACACTTCACAAGTACCACCACGACG | 120 |
| FH_P1 | ACCGCCTCCCTCGCGACGGGACTCACCGTAGTGGGACACTTCACAAGTACCACCACGACG | 120 |
|  | ************************************************************ |  |
| M129_P1 | CTCAAGCGCCAGCAATTTAGCTACACCCGCCCTGACGAGGTCGCGCTGCGCCACACCAAT | 180 |
| FH_P1 | CTCAAGCGCCAGCAATTTAGCTACACCCGCCCTGACGAGGTCGCGCTGCGCCACACCAAT | 180 |
|  | ************************************************************ |  |
| M129_P1 | GCCATCAACCCGCGCTTAACCCCGTGAACGTATCGTAACACGAGCTTTTCCTCCCTCCCC | 240 |
| FH_P1 | GCCATCAACCCGCGCTTAACCCCGTGAACGTATCGTAACACGAGCTTTTCCTCCCTCCCC | 240 |
|  | ************************************************************ |  |
| M129_P1 | CTCACGGGTGAAAATCCCGGGGCGTGGGCCTTAGTGCGCGACAACAGCGCTAAGGGCATC | 300 |
| FH_P1 | CTCACGGGTGAAAATCCCGGGGCGTGGGCCTTAGTGCGCGACAACAGCGCTAAGGGCATC | 300 |
|  | ************************************************************ |  |
| M129_P1 | ACTGCCGGCAGTGGCAGTCAACAAACCACGTATGATCCCACCCGAACCGAAGCGGCTTTG | 360 |
| FH_P1 | ACTGCCGGCAGTGGCAGTCAACAAACCACGTATGATCCCACCCGAACCGAAGCGGCTTTG | 360 |
|  | ************************************************************ |  |
| M129_P1 | ACCGCATCAACCACCTTTGCGTTACGCCGGTATGACCTCGCCGGGCGCGCCTTATACGAC | 420 |
| FH_P1 | ACCGCATCAACCACCTTTGCGTTACGCCGGTATGACCTCGCCGGGCGCGCCTTATACGAC | 420 |
|  | ************************************************************ |  |
| M129_P1 | CTCGATTTTTCGAAGTTAAACCCGCAAACGCCCACGCGCGACCAAACCGGGCAGATCACC | 480 |
| FH_P1 | CTCGATTTTTCGAAGTTAAACCCGCAAACGCCCACGCGCGACCAAACCGGGCAGATCACC | 480 |
|  | ************************************************************ |  |
| M129_P1 | TTTAACCCCTTTGGCGGCTTTGGTTTGAGTGGGGCTGCACCCCAACAGTGAAACGAGGTC | 540 |
| FH_P1 | TTTAACCCCTTTGGCGGCTTTGGTTTGAGTGGGGCTGCACCCCAACAGTGAAACGAGGTC | 540 |
|  | ************************************************************ |  |
| M129_P1 | AAAAACAAGGTCCCCGTCGAGGTGGCGCAAGACCCCTCCAATCCCTACCGGTTTGCCGTT | 600 |
| FH_P1 | AAAAACAAGGTCCCCGTCGAGGTGGCGCAAGACCCCTCCAATCCTTATCGGTTTGCCGTT | 600 |
|  | ********************************************** ** ********** |  |
| M129_P1 | TTACTCGTGCCGCGCAGCGTGGTGTACTATGAGCAGTTGCAAAGGGGGTTGGGCTTACCA | 660 |
| FH_P1 | TTACTCGTGCCGCGTAGCGTGGTGTACTATGAGCAGTTGCAGCGGGGGTTAGCGCTCCCT | 660 |
|  | ************** ***************************** * * ** |  |
| M129_P1 | CAGCAGCGAACCGAGAGTGGTCAAAATACTTCCACC----ACCGGGGCAATGTTTGGCTTG | 717 |
| FH_P1 | AACCAAGGGAGTTCGTCAGGCTCAGACAGCACTAACCAAACAGGCGCAATGTTTGGCTTG | 720 |
|  | * ** * * * ** *** * ** ** **************** |  |

Figure 5

```
M129_P1   AAGGTGAAGAACGCCGAGGCGGACACCGCGAAG---AGCAATGAAAAACTCCA-GGGCGCT   774
FH_P1     AAGGTGAAGGATGCAACCGTGGATAGTTCGAAGCAATCAACGGAAAGCTTAAAGGGCGAA   780
          ******** * **    * *** *  *****  * *** * *** **  * *****

M129_P1   GAGGCCACTGGTTCTTCAACCACATCTGGATCTGGCCAATCCACCCAACGTGGGGGTTCG   834
FH_P1     GAATCGAGTTCCAGTTCCACCACATCT----TCCACCTCCACCCACCCAACGTGGGGGTTCG   837
          **  * * *   *** ********   **   * ********************

M129_P1   TCAGGGACACCAAAGTCAAGGCTTTAAAAATAGAGGTGAAAAAGAAATC----GGACTCGG   892
FH_P1     TCAAATGAAAACAAAGTCAAGGCGTTGCAGGTGGCGGTGAAAAAGAAATCCGGGAGTCAG   897
          ***   ** * *********** **  *   * * *************  *** ** *

M129_P1   AG---------------GACAATGGTCAGCTGCAGTTAGAAAAAAATGATCTCGCCAAC   936
FH_P1     GGCAACTCCGGTGACCAAGGCACCGAACAGGTGGAACTTGAATCTAATGATTTAGCCAAC   957
           *              * **  *   *** ** *  * ***** *  ******

M129_P1   GCTCCCATTAAGCGGAGCGAGGAGTCGGGTCAGTCCGTCCAACTCAAGGCGGACGATTTT   996
FH_P1     GCCCCGATTAAACGGGGCTCCAATAACAACCAGCAAGTCCAACTCAAGGCGGACGATTTT   1017
          ** ** *****  ***   **   *       ***  ***********************

M129_P1   GGTACTGCCCTTTCCAGTTCGGGATCAGGCGGCAACTCCAATCCCGGTTCCCCCACCCCC   1056
FH_P1     GGTACTGCCCCTTCCAGTTCGGGATCAGGCA---------CCCAAGATGGCACCCCCACCCCC   1071
          ********** ******************    ** *   ** **********

M129_P1   TGAAGGCCGTGGCTTGCGACTGAGCAAATTCACAAGGACCTCCCCAAATGATCCGCCTCG   1116
FH_P1     TGAACGCCGTGGTTAACGACTGAGCAAATTCACAACGACCCCGCCAAATTCGCCGCCTCG   1131
          **** *******  * ******************* ****  ** ****  * *******

M129_P1   ATCCTGATTCTGTACGATGCGCCTTATGCGCGCAACCGTACCGCCATTGACCGCGTTGAT   1176
FH_P1     ATCCTGATTCTGTACGATGCGCCTTATGCGCGCAACCGTACCGCCATTGACCGCGTTGAT   1191
          ************************************************************

M129_P1   CACTTGGATCCCAAGGCCATGACCGCGAACTATCCGCCCAGTTGAAGAACGCCCAAGTGA   1236
FH_P1     CACTTGGATCCCAAGGCCATGACCGCGAACTATCCGCCCAGTTGAAGAACGCCCAAGTGA   1251
          ************************************************************

M129_P1   AACCACCACGGTTTGTGGGACTGAAAGGCGCGCGATGTTTTGCTCCAAACCACCGGGTTC   1296
FH_P1     AACCACCACGGTTTGTGGGACTGAAAGGCGCGCGATGTTTTGCTCCAAACCACCGGGTTC   1311
          ************************************************************

M129_P1   TTCAACCCGCGCCGCCACCCCGAGTGGTTTGATGGCGGGCAGACGGTCGCGGATAACGAA   1356
FH_P1     TTCAACCCGCGCCGCCACCCCGAGTGGTTTGATGGCGGGCAGACGGTCGCGGATAACGAA   1371
          ************************************************************

M129_P1   AAGACCGGGTTTGATGTGGATAACTCTGAAAACACCAAGCAGGGCTTTCAAAAGGAAGCT   1416
FH_P1     AAGACCGGGTTTGATGTGGATAACTCTGAAAACACCAAGCAGGGCTTTCAAAAGGAAGCT   1431
          ************************************************************
```

Figure 6

| | | |
|---|---|---|
| M129_P1 | GACTCCGACAAGTCGGCCCCGATCGCCCTCCCGTTTGAAGCGTACTTCGCCAACATTGGC | 1476 |
| FH_P1 | GACTCCGACAAGTCGGCCCCGATCGCCCTCCCGTTTGAAGCGTACTTCGCCAACATTGGC | 1491 |
| | ************************************************************ | |
| M129_P1 | AACCTCACCTGGTTCGGGCAAGCGCTTTTGGTGTTTGGTGGCAATGGCCATGTTACCAAG | 1536 |
| FH_P1 | AACCTCACCTGGTTCGGGCAAGCGCTTTTGGTGTTTGGTGGCAATGGCCATGTTACCAAG | 1551 |
| | ************************************************************ | |
| M129_P1 | TCGGCCCACACCGCGCCTTTGAGTATAGGTGTCTTTAGGGTGCGCTATAATGCAACTGGT | 1596 |
| FH_P1 | TCGGCCCACACCGCGCCTTTGAGTATAGGTGTCTTTAGGGTGCGCTATAATGCAACTGGT | 1611 |
| | ************************************************************ | |
| M129_P1 | ACCAGTGCTACTGTAACTGGTTGACCATATGCCTTACTGTTCTCAGGCATGGTCAACAAA | 1656 |
| FH_P1 | ACCAGTGCTACTGTAACTGGTTGACCATATGCCTTACTGTTCTCAGGCATGGTCAACAAA | 1671 |
| | ************************************************************ | |
| M129_P1 | CAAACTGACGGGTTAAAGGATCTACCCTTTAACAATAACCGCTGGTTTGAATATGTACCA | 1716 |
| FH_P1 | CAAACTGACGGGTTAAAGAATCTACCCTTTAACAATAACCGCTGGTTTGAATATGTACCA | 1731 |
| | ****************** ***************************************** | |
| M129_P1 | CGGATGGCAGTTGCTGGCGCTAAGTTCGTTGGTAGGGAACTCGTTTTAGCGGGTACCATT | 1776 |
| FH_P1 | CGGATGGCAGTTGCTGGCGCTAAGTTCGTTGGTAGGGAACTCGTTTTAGCGGGTACCATT | 1791 |
| | ************************************************************ | |
| M129_P1 | ACCATGGGTGATACCGCTACCGTACCTCGCTTACTGTACGATGAACTTGAAAGCAACCTG | 1836 |
| FH_P1 | ACCATGGGTGATACCGCTACCGTACCTCGCTTACTGTACGATGAACTTGAAAGCAACCTG | 1851 |
| | ************************************************************ | |
| M129_P1 | AACTTAGTAGCGCAAGGCCAAGGTCTTTTACGCGAAGACTTGCAACTCTTCACACCCTAC | 1896 |
| FH_P1 | AACTTAGTAGCGCAAGGCCAAGGTCTTTTACGCGAAGACTTGCAACTCTTCACACCCTAC | 1911 |
| | ************************************************************ | |
| M129_P1 | GGATGAGCCAATCGTCCGGATTTACCAATCGGGGCTTGAAGTAGTAGTAGTAGTAGTAGT | 1956 |
| FH_P1 | GGATGAGCCAATCGTCCGGATTTACCAATCGGGGCTTGAAGTAGTAGTAGTAGTA----GT | 1968 |
| | ******************************************************    ** | |
| M129_P1 | CACAACGCACCCTACTACTTCCACAATAACCCCGATTGACAAGACCGTCCAATCCAAAAT | 2016 |
| FH_P1 | CACAACGCACCCTACTACTTCCACAATAACCCCGATTGACAAGACCGTCCAATCCAAAGT | 2028 |
| | *********************************************************** * | |
| M129_P1 | GTGGTTGATGCCTTTATTAAGCCCTGAGAGGACAAGAACGGTAAGGATGATGCCAAATAC | 2076 |
| FH_P1 | GTGGTTGATGCCTTTATTAAGCCCTGAGAGGACAAGAACGGTAAGGATGATGCCAAATAC | 2088 |
| | ************************************************************ | |
| M129_P1 | ATCTACCCTTACCGTTACAGTGGCATGTGAGCTTGACAGGTATACAACTGGTCCAATAAG | 2136 |
| FH_P1 | ATCTACCCTTACCGTTACAGTGGCATGTGAGCTTGACAGGTATACAACTGGTCCAATAAG | 2148 |
| | ************************************************************ | |

Figure 7

```
M129_P1    CTCACTGACCAACCATTAAGTGCTGACTTTGTCAATGAGAATGCTTACCAACCAAACTCC    2196
FH_P1      CTCACTGACCAACCATTAAGTGCTGACTTTGTCAATGAGAATGCTTACCAACCAAACTCC    2208
           ************************************************************

M129_P1    TTGTTTGCTGCTATTCTCAATCCGGAATTGTTAGCAGCTCTTCCCGACAAGGTTAAATAC    2256
FH_P1      TTGTTTGCTGCTATTCTCAATCCGGAATTGTTAGCAGCTCTTCCCGACAAGGTTAAATAC    2268
           ************************************************************

M129_P1    GGTAAGGAAAACGAGTTTGCTGCTAACGAGTACGAGCGCTTTAACCAGAAGTTAACGGTA    2316
FH_P1      GGTAAGGAAAACGAGTTTGCTGCTAACGAGTACGAGCGCTTTAACCAGAAGTTAACGGTA    2328
           ************************************************************

M129_P1    GCTCCTACCCAAGGAACAAACTGATCCCACTTCTCCCCCACGCTTTCCCGTTTCTCCACC    2376
FH_P1      GCTCCTACCCAAGGAACAAACTGATCCCACTTCTCCCCCACGCTTTCCCGTTTCTCCACC    2388
           ************************************************************

M129_P1    GGGTTCAACCTTGTGGGGTCGGTGCTCGACCAGGTGTTGGATTATGTGCCCTGGATTGGG    2436
FH_P1      GGGTTCAACCTTGTGGGGTCGGTGCTCGACCAGGTGTTGGATTATGTGCCCTGGATTGGG    2448
           ************************************************************

M129_P1    AATGGGTACAGGTATGGCAATAACCACCGGGGCGTGGATGATATAACCGCGCCTCAAACC    2496
FH_P1      AATGGGTACAGGTATGGCAATAACCACCGGGGCGTGGATGATATAACCGCGCCTCAAACC    2508
           ************************************************************

M129_P1    AGCGCGGGGTCGTCCAGCGGAATTAGTACGAACACAAGTGGTTCGCGTTCCTTTCTCCCG    2556
FH_P1      AGCGCGGGGTCGTCCAGCGGAATTAGTACGAACACAAGTGGTTCGCGTTCCTCTCTCCCG    2568
           **************************************************** ******

M129_P1    ACGTTTTCCAACATCGGCGTCGGCCTCAAAGCGAATGTCCAAGCCACCCTCGGGGGCAGT    2616
FH_P1      ACGTTTTCCAACATCGGCGTCGGCCTCAAAGCGAATGTCCAAGCCACCCTCGGGGGCAGT    2628
           ************************************************************

M129_P1    CAGACGATGATTACAGGCGGTTCGCCTCGAAGAACCCTCGACCAAGCCAACCTCCAGCTC    2676
FH_P1      CAGACGATGATTACAGGCGGTTCGCCTCGAAGAACCCTCGACCAAGCCAACCTCCAGCTC    2688
           ************************************************************

M129_P1    TGAACGGGGGCGGGGTGAAGGAATGATAAGGCTTCAAGTGGACAAAGTGACGAAAACCAC    2736
FH_P1      TGAACGGGGGCGGGGTGAAGGAATGATAAGGCTTCAAGTGGACAAAGTGACGA----CCAC    2745
           *****************************************************    ****

M129_P1    ACCAAGTTCACGAGCGCTACGGGGATGGACCAGCAGGGACAATCAGGTACCTCCGCGGGG    2796
FH_P1      ACCAAGTTCACGAGCGCTACGGGGATGGGCCAGCAGGAACAATCAGGTACCTCCGCGGGG    2805
           ****************************  ******** ********************

M129_P1    AATCCCGACTCGTTAAAGCAGGATAATATTAGTAAGAGTGGGGATAGTTTAACCACGCAG    2856
FH_P1      AATCCCGACTCGTTAAAGCAGGATAAGATTAGTAAGAGTGGGGATAGTTTAACCACGCAG    2865
           ************************** ********************************
```

Figure 8

```
M129_P1    GACGGCAATGCGATCGATCAACAAGAGGCCACCAACTACACCAACCTCCCCCCCAACCTC    2916
FH_P1      GACGGCAATGCGATGGATCAACAAGAGGCCACCAACTACACCAACCTCCCCCCCAACCTC    2925
           *************  *********************************************

M129_P1    ACCCCCACCGCTGATTGACCGAACGCGCTGTCATTCACCAACAAGAACAACGCGCAGCGC    2976
FH_P1      ACCCCCACCGCTGATTGACCGAACGCGCTGTCATTCACCAACAAGAACAACGCGCAGCGC    2985
           ************************************************************

M129_P1    GCCCAGCTCTTCCTCCGCGGCTTGTTGGGCAGCATCCCGGTGTTGGTGAATCGAAGTGGG    3036
FH_P1      GCCCAGCTGTTCCTGCGCGGCCTGTTGGGCAGCATCCCGGTGTTGGTTAATAAGTCCGGC    3045
           ********  *****  ***** ***********************  *** **

M129_P1    TCCGATTCCAACA----AATTCCAAGCCACCGACCAAAAATGGTCCTACACCGACTTACAT    3093
FH_P1      CAAGATGATAACAGTAAGTTTAAGGCGGAGGACCAAAAATGGTCCTACACCGACTTACAG    3105
             *** ****  *  ** *  *********************

M129_P1    TCGGACCAAACCAAACTGAACCTCCCCGCTTACGGTGAGGTGAATGGGTTGTTGAATCCG    3153
FH_P1      TCGGACCAAACCAAACTGAACCTCCCCGCTTACGGTGAGGTGAATGGGTTGTTGAATCCG    3165
           ************************************************************

M129_P1    GCGTTGGTGGAAACCTATTTTGGGAACACGCGAGCGGGTGGTTCGGGGTCCAACACGACC    3213
FH_P1      GCGTTGGTGGAAACCTATTTTGGGAACACGCGAGCGAGTGGTTCGGGGTCCAACACGACC    3225
           ************************************ ***********************

M129_P1    AGTTCACCCGGTATCGGTTTTAAAATTCCCGAACAAAATA-------------ATGAT-TCCAAA    3264
FH_P1      AGTTCACCCGGTATCGGTTTTAAAATTCCCGAACAAAGTGGCACAAACACAACGTCGAAG    3285
           *************************************  *       *  * ** **

M129_P1    GCCACCCTGATCACCCCCGGGTTGGCTTGAACGCCCCAGGACGTCGGTAACCTCGTTGTC    3324
FH_P1      GCTGTGCTGATCACCCCCGGGTTGGCTTGAACGCCGCAAGACGTTGGTAACCTCGTTGTC    3345
           **  ***************************** ** *****  ***************

M129_P1    AGTGGCACCACGGTGAGCTTCCAGCTCGGCGGGTGGCTGGTCACCTTCACGGACTTTGTC    3384
FH_P1      AGTGGCACCAGCTTCAGCTTCCAGCTCGGCGGGTGGTTAGTTACGTTCACGGACTTTATC    3405
           **********  * ********************  * ** **  ********** **

M129_P1    AAACCCCGCGCGGGTTACCTCGGTCTCCAGTTAACGGGCTTGGATGCAAGTGATGCGACG    3444
FH_P1      AAACCCCGCGCTGGTTACCTCGGGCTCCAGTTAACGGGCTTGGATGCAAGTGATGCGACG    3465
           ***********  **********  ***********************************

M129_P1    CAGCGCGCCCTCATTTGGGCCCCCCGGCCCTGAGCGGCCTTTCGTGGCAGTTGGGTCAAC    3504
FH_P1      CAGCGCGCTCTCATTTGGGCCCCCCGGCCCTGAGCGGCCTTTCGTGGCAGTTGGGTCAAC    3525
           ********  **************************************************

M129_P1    CGGTTGGGCCGCGTGGAGAGTGTGTGGGATTTGAAGGGGGTGTGGGCGGATCAAGCTCAG    3564
FH_P1      CGGTTGGGCCGCGTGGAGAGTGTGTGGGATTTGAAGGGGGTGTGGGCGGATCAAGCTCAG    3585
           ************************************************************
```

Figure 9

```
M129_P1    TCCGACTCGCAAGGATCTACCACCACCGCAACAAGGAACGCCTTACCGGAGCACCCGAAT    3624
FH_P1      TCCGACTCGCAAGGATCTACCACCACCGCAACAAGGGACGCCTTACCGGAGCACCCGAAT    3645
           ****************************************  *****************

M129_P1    GCTTTGGCCTTTCAGGTGAGTGTGGTGGAAGCGAGTGCTTACAAGCCAAACACGAGCTCC    3684
FH_P1      GCTTTGGCCTTTCAGGTGAGTGTGGTGGAAGCGAGTGCTTACAAGCCAAACACGAGCTCC    3705
           ************************************************************

M129_P1    GGCCAAACCCAATCCACTAACAGTTCCCCCTACCTGCACTTGGTGAAGCCTAAGAAAGTT    3744
FH_P1      GGCCAAACCCAATCCACTAACAGTTCCCCCTACCTGCACTTGGTGAAGCCTAAGAAAGTT    3765
           ************************************************************

M129_P1    ACCCAATCCGACAAGTTAGACGACGATCTTAAAAACCTGTTGGACCCCAACCAGGTTCGC    3804
FH_P1      ATCCAATCCGACAAGTTAGACGACGATCTTAAAAACCTGTTGGACCCCAACCAGGTTCGC    3825
           *  *********************************************************

M129_P1    ACCAAGCTGCGCCAAAGCTTTGGTACAGACCATTCCACCCAGCCCCAGCCCCAATCGCTC    3864
FH_P1      ACCAAGCTGCGCCAAAGCTTTGGTACAGACCATTCCACCCAGCCCCAGCCCCAATCGCTC    3885
           ************************************************************

M129_P1    AAAACAACGACACCGGTATTTGGGACGAGTAGTGGTAACCTCAGTAGTGTGCTTAGTGGT    3924
FH_P1      AAAACAACGACACCGGTATTTGGGACGAGTAGTGGTAACCTCAGTAGTGTGCTTAGTGGT    3945
           ************************************************************

M129_P1    GGGGGTGCTGGAGGGGGTTCTTCAGGCTCAGGTCAATCTGGCGTGGATCTCTCCCCCGTT    3984
FH_P1      GGGGGTGCTGGAGGGGGTTCTTCAGGCTCAGGTCAATCTGGCGTGGATCTCTCCCCCGTT    4005
           ************************************************************

M129_P1    GAAAAAGTGAGTGGGTGGCTTGTGGGGCAGTTACCAAGCACGAGTGACGGAAACACCTCC    4044
FH_P1      GAAAAAGTGAGTGGGTGGCTTGTGGGGCAGTTACCAAGCACGAGTGACGGAAACACCTCC    4065
           ************************************************************

M129_P1    TCCACCAACAACCTCGCGCCTAATACTAATACGGGGAATGATGTGGTGGGGGTTGGTCGA    4104
FH_P1      TCCACCAACAACCTCGCGCCTAATACTAATACGGGGAATGATGTGGTGGGGGTTGGTCGA    4125
           ************************************************************

M129_P1    CTTTCTGAAAGCAACGCCGCAAAGATGAATGACGATGTTGATGGTATTGTACGCACCCCA    4164
FH_P1      CTTTCTGAAAGCAACGCCGCAAAGATGAACGACGATGTTGATGGTATTGTACGCACCCCA    4185
           ***************************** ******************************

M129_P1    CTCGCTGAACTGTTAGATGGGGAAGGACAAACAGCTGACACTGGTCCACAAAGCGTGAAG    4224
FH_P1      CTCGCTGAACTGTTAGATGGGGAAGGACAAACAGCTGACACTGGTCCACAAAGCGTGAAG    4245
           ************************************************************

M129_P1    TTCAAGTCTCCTGACCAAATTGACTTCAACCGCTTGTTTACCCACCCAGTCACCGATCTG    4284
FH_P1      TTCAAGTCTCCTGACCAAATTGACTTCAACCGCTTGTTTACCCACCCAGTCACCGATCTG    4305
           ************************************************************
```

Figure 10

| M129_P1 | TTTGATCCGGTAACTATGTTGGTGTATGACCAGTACATACCGCTGTTTATTGATATCCCA | 4344 |
| FH_P1 | TTTGATCCGGTAACTATGTTGGTGTATGACCAGTACATACCGCTGTTTATTGATATCCCA | 4365 |
| | ************************************************************ | |
| M129_P1 | GCAAGTGTGAACCCTAAAATGGTTCGTTTAAAGGTCTTGAGCTTTGACACCAACGAACAG | 4404 |
| FH_P1 | GCAAGTGTGAACCCTAAAATGGTTCGTTTAAAGGTCTTGAGCTTTGACACCAACGAACAG | 4425 |
| | ************************************************************ | |
| M129_P1 | AGCTTAGGTCTCCGCTTAGAGTTCTTTAAACCTGATCAAGATACCCAACCAAACAACAAC | 4464 |
| FH_P1 | AGCTTAGGTCTCCGCTTAGAGTTCTTTAAACCTGATCAAGATACCCAACCAAACAACAAC | 4485 |
| | ************************************************************ | |
| M129_P1 | GTTCAGGTCAATCCGAATAACGGTGACTTCTTACCACTGTTAACGGCCTCCAGTCAAGGT | 4524 |
| FH_P1 | GTTCAGGTCAATCCGAATAACGGTGACTTCTTACCACTGTTAACGGCCTCCAGTCAAGGT | 4545 |
| | ************************************************************ | |
| M129_P1 | CCCCAAACCTTGTTTAGTCCGTTTAACCAGTGACCTGATTACGTGTTGCCGTTAGCGATC | 4584 |
| FH_P1 | CCCCAAACCTTGTTTAGTCCGTTTAACCAGTGACCTGATTACGTGTTGCCGTTAGCGATC | 4605 |
| | ************************************************************ | |
| M129_P1 | ACTGTACCTATTGTTGTGATTGTGCTCAGTGTTACCTTAGGACTTGCCATTGGAATCCCA | 4644 |
| FH_P1 | ACTGTACCTATTGTTGTGATTGTGCTCAGTGTTACCTTAGGACTTGCCATTGGAATCCCA | 4665 |
| | ************************************************************ | |
| M129_P1 | ATGCACAAGAACAAACAGGCCTTGAAGGCTGGGTTTGCGCTATCAAACCAAAAGGTTGAT | 4704 |
| FH_P1 | ATGCACAAGAACAAACAGGCCTTGAAGGCTGGGTTTGCGCTATCAAACCAAAAGGTTGAT | 4725 |
| | ************************************************************ | |
| M129_P1 | GTGTTGACCAAAGCGGTTGGTAGTGTCTTTAAGGAAATCATTAACCGCACAGGTATCAGT | 4764 |
| FH_P1 | GTGTTGACCAAAGCGGTTGGTAGTGTCTTTAAGGAAATCATTAACCGCACAGGTATCAGT | 4785 |
| | ************************************************************ | |
| M129_P1 | CAAGCGCCAAAACGCTTGAAACAAACCAGTGCGGCTAAACCAGGAGCACCCCGCCCACCA | 4824 |
| FH_P1 | CAAGCGCCAAAACGCTTGAAACAAACCAGTGCGGCTAAACCAGGAGCACCCCGCCCACCA | 4845 |
| | ************************************************************ | |
| M129_P1 | GTACCACCAAAGCCAGGGGCTCCTAAGCCACCAGTGCAACCACCTAAAAAACCCGCTTAG | 4884 |
| FH_P1 | GTACCACCAAAGCCAGGGGCTCCTAAGCCACCAGTGCAACCACCTAAAAAACCCGCTTAG | 4905 |

SEQUENCE LISTING

```
<160> NUMBER OF SEQ ID NOS: 8

<210> SEQ ID NO 1
<211> LENGTH: 10
<212> TYPE: PRT
<213> ORGANISM: Mycoplasma pneumoniae

<400> SEQUENCE: 1

Ser Thr Asp Asn Gly Leu Ile Ile Gly Ile
1               5                   10

<210> SEQ ID NO 2
<211> LENGTH: 20
<212> TYPE: DNA
<213> ORGANISM: Mycoplasma pneumoniae

<400> SEQUENCE: 2
tggggagcaa ayaggattag                                              20

<210> SEQ ID NO 3
<211> LENGTH: 25
<212> TYPE: DNA
<213> ORGANISM: Mycoplasma pneumoniae

<400> SEQUENCE: 3
caccatctgt cactctgtta acctc                                        25

<210> SEQ ID NO 4
<211> LENGTH: 23
<212> TYPE: DNA
<213> ORGANISM: Mycoplasma pneumoniae

<400> SEQUENCE: 4
```

```
ctcaaacgct aaaagtgcta acg                                          23
```

<210> SEQ ID NO 5
<211> LENGTH: 27
<212> TYPE: DNA
<213> ORGANISM: Mycoplasma pneumoniae

<400> SEQUENCE: 5

```
aaaccattat tacaggtcaa ataagac                                      27
```

<210> SEQ ID NO 6
<211> LENGTH: 1788
<212> TYPE: DNA
<213> ORGANISM: Mycoplasma pneumoniae

<400> SEQUENCE: 6

```
atgagtacag ataacggctt aattatcggc attgaccttg gtaccactaa ctcctgtgtg    60
tcggtcatgg agaatggacg cccagtagtg ttggaaaacc ctgaaggtaa acgcaccacc   120
ccttcgattg tttcttacaa gaacaacgaa attattgtgg gtgatgctgc gaaacggcaa   180
atggtaacta accctaatac tattgttttcc attaagcgtt taatgggtac ctccaataag   240
gtaaccgtta agaatcctga tggttctacc aaagagttaa ctcctgaaga ggtatcagcg   300
caaatcttga gctacctcaa ggactatgcg gaaaagaaga ttggtaaaac gatttcccgt   360
gctgttatta ccgtacctgc ttactttaac gatgcagaac ggaacgctac taaaaccgct   420
ggtaagattc tggttttaaa cgttgagcgg attattaacg aacctaccgc cgctgcattg   480
gcttatggga tcgacaagtc taaccgagaa atgaaagtct tggtgtacga ccttggtggt   540
ggtaccttttg acgtttcctt acttgacatt gctgaaggta ccttcgaagt attagccact   600
gctggggaca accgtttggg tggtgatgac tgggacaaca agattattga gttcatctta   660
gcgcacattg cccaagaaca caatgggctt aacttgtcca atgacaagat ggctatgcaa   720
cgcttaaagg aagcggctga acgtgctaag attgaacttt ccgcccaact agaagcaatt   780
atctctttac cgttcttaac ggttaccgaa aagggtccgg taaacgttga acttaagcta   840
acccgtgcta agtttgaaga attaccaaa caattactag aacgtactcg caacccaatt   900
tcggatgttt acgtgaagc caagattaaa ccagaagaaa ttaatgaaat cttgttggtg   960
ggtggatcga cccggatgcc agcagtgcaa aaactagtgg aatcaatggt accaggacac  1020
agtccaaacc gctcaattaa cccggatgag gtggtagcca ttggtgctgc catccaaggg  1080
ggtgtgttac gcggtgatgt aaaggacgtg ttactgttgg acgttactcc tttaacgctc  1140
tcgattgaaa cccttggtgg tgtagcaact ccgttaatta agcgtaacac caccattcct  1200
gtaagtaaga gtcaaatctt ctctacagcg caagacaacc aagaatcagt ggatgtggtg  1260
gtttgtcaag gggaacgccc aatggcacgt gacaacaagt cttttgggtcg ctttaactta  1320
gggggcatcc aaccagcacc caagggtaaa ccccaaattg aaattacctt tagcttggac  1380
gccaacggga tcttaaacgt gaaggctaaa gatttaacca ctcaaaagga aaacagtatt  1440
actattagtg acaacggcaa cttgtccgaa gaggaaatcc aaaagatgat tcgtgatgcg  1500
gaagccaaca aggagcgtga caatgtgatt cgtgaacgca ttgagctccg taacgaaggt  1560
gaaagcatcg tgagcacgat taaggagatt ctccaaagtc ccgaagcgaa ggacttccct  1620
aaagaagaga aggaaaaact cgacaagatt accggtggta ttgatgcagc aattaaggcc  1680
aatgactaca ccaagttaaa agccgaaatc gaaaacttca agaagtgaag ggaagaaatg  1740
```

-continued

| | |
|---|---|
| gccaagaagt acaaccctaa cggggatcaa ggtcaaccag cacaataa | 1788 |

<210> SEQ ID NO 7
<211> LENGTH: 4884
<212> TYPE: DNA
<213> ORGANISM: Mycoplasma pneumoniae

<400> SEQUENCE: 7

| | |
|---|---|
| atgcaccaaa ccaaaaaaac tgccttgtcc aagtccactt ggattctcat cctcaccgcc | 60 |
| accgcctccc tcgcgacggg actcaccgta gtgggacact tcacaagtac caccacgacg | 120 |
| ctcaagcgcc agcaatttag ctacaccgc cctgacgagg tcgcgctgcg ccacaccaat | 180 |
| gccatcaacc cgcgcttaac cccgtgaacg tatcgtaaca cgagcttttc ctccctcccc | 240 |
| ctcacgggtg aaaatcccgg ggcgtgggcc ttagtgcgcg acaacagcgc taagggcatc | 300 |
| actgccggca gtggcagtca acaaaccacg tatgatccca cccgaaccga agcggctttg | 360 |
| accgcatcaa ccacctttgc gttacgccgg tatgacctcg ccgggcgcgc cttatacgac | 420 |
| ctcgattttt cgaagttaaa cccgcaaacg cccacgcgcg accaaaccgg gcagatcacc | 480 |
| tttaacccct ttggcggctt tggtttgagt ggggctgcac cccaacagtg aaacgaggtc | 540 |
| aaaaacaagg tccccgtcga ggtggcgcaa gaccccctcca atccctaccg gtttgccgtt | 600 |
| ttactcgtgc cgcgcagcgt ggtgtactat gagcagttgc aaaggggggtt gggcttacca | 660 |
| cagcagcgaa ccgagagtgg tcaaaatact tccaccaccg gggcaatgtt tggcttgaag | 720 |
| gtgaagaacg ccgaggcgga caccgcgaag agcaatgaaa aactccaggg cgctgaggcc | 780 |
| actggttctt caaccacatc tggatctggc caatccaccc aacgtggggg ttcgtcaggg | 840 |
| gacaccaaag tcaaggcttt aaaaatagag gtgaaaaaga atcggactc ggaggacaat | 900 |
| ggtcagctgc agttagaaaa aaatgatctc gccaacgctc ccattaagcg gagcgaggag | 960 |
| tcgggtcagt ccgtccaact caaggcggac gattttggta ctgcccttttc cagttcggga | 1020 |
| tcaggcggca actccaatcc cggttccccc acccccctgaa ggccgtggct tgcgactgag | 1080 |
| caaattcaca aggacctccc caaatgatcc gcctcgatcc tgattctgta cgatgcgcct | 1140 |
| tatgcgcgca accgtaccgc cattgaccgc gttgatcact tggatcccaa ggccatgacc | 1200 |
| gcgaactatc cgcccagttg aagaacgccc aagtgaaacc accacggttt gtgggactga | 1260 |
| aaggcgcgcg atgttttgct ccaaaccacc gggttcttca acccgcgccg ccaccccgag | 1320 |
| tggtttgatg gcgggcagac ggtcgcggat aacgaaaaga ccgggtttga tgtggataac | 1380 |
| tctgaaaaca ccaagcaggg cttttcaaaag gaagctgact ccgacaagtc ggccccgatc | 1440 |
| gccctcccgt ttgaagcgta cttcgccaac attggcaacc tcacctggtt cgggcaagcg | 1500 |
| cttttggtgt ttggtggcaa tggccatgtt accaagtcgg cccacaccgc gcctttgagt | 1560 |
| ataggtgtct ttagggtgcg ctataatgca actggtacca gtgctactgt aactggttga | 1620 |
| ccatatgcct tactgttctc aggcatggtc aacaaacaaa ctgacgggtt aaaggatcta | 1680 |
| cccctttaaca ataaccgctg gtttgaatat gtaccacgga tggcagttgc tggcgctaag | 1740 |
| ttcgttggta gggaactcgt tttagcgggt accattacca tgggtgatac cgctaccgta | 1800 |
| cctcgcttac tgtacgatga acttgaaagc aacctgaact tagtagcgca aggccaaggt | 1860 |
| cttttacgcg aagacttgca actcttcaca ccctacggat gagccaatcg tccggattta | 1920 |
| ccaatcgggg cttgaagtag tagtagtagt agtagtcaca acgcaccccta ctacttccac | 1980 |
| aataaccccg attgacaaga ccgtccaatc caaaatgtgg ttgatgcctt tattaagccc | 2040 |
| tgagaggaca agaacggtaa ggatgatgcc aaatacatct accccttaccg ttacagtggc | 2100 |

```
atgtgagctt gacaggtata caactggtcc aataagctca ctgaccaacc attaagtgct    2160
gactttgtca atgagaatgc ttaccaacca aactccttgt ttgctgctat tctcaatccg    2220
gaattgttag cagctcttcc cgacaaggtt aaatacggta aggaaaacga gtttgctgct    2280
aacgagtacg agcgctttaa ccagaagtta acggtagctc ctacccaagg aacaaactga    2340
tcccacttct cccccacgct ttcccgtttc tccaccgggt tcaaccttgt ggggtcggtg    2400
ctcgaccagg tgttggatta tgtgccctgg attgggaatg ggtacaggta tggcaataac    2460
caccggggcg tggatgatat aaccgcgcct caaaccagcg cggggtcgtc cagcggaatt    2520
agtacgaaca aagtggttc gcgttccttt ctcccgactt tttccaacat cggcgtcggc     2580
ctcaaagcga atgtccaagc caccctcggg ggcagtcaga cgatgattac aggcggttcg    2640
cctcgaagaa ccctcgacca agccaacctc cagctctgaa cggggggcggg gtgaaggaat   2700 gataaggctt caagtggaca aagtgacgaa aaccacacca agttcacgag cgctacgggg   2760
atggaccagc agggacaatc aggtacctcc gcggggaatc ccgactcgtt aaagcaggat   2820
aatattagta agagtgggga tagtttaacc acgcaggacg gcaatgcgat cgatcaacaa    2880
gaggccacca actacaccaa cctcccccccc aacctcaccc ccaccgctga ttgaccgaac   2940
gcgctgtcat tcaccaacaa gaacaacgcg cagcgcgccc agctcttcct ccgcggcttg    3000
ttgggcagca tcccggtgtt ggtgaatcga agtgggtccg attccaacaa attccaagcc   3060
accgaccaaa aatggtccta caccgactta cattcggacc aaaccaaact gaacctcccc    3120
gcttacggtg aggtgaatgg gttgttgaat ccggcgttgg tggaaaccta ttttgggaac    3180
acgcgagcgg gtggttcggg gtccaacacg accagttcac ccggtatcgg ttttaaaatt    3240
cccgaacaaa ataatgattc caaagccacc ctgatcaccc ccgggttggc ttgaacgccc    3300
caggacgtcg gtaacctcgt tgtcagtggc accacggtga gcttccagct cggcgggtgg    3360
ctggtcacct tcacggactt tgtcaaaccc cgcgcgggtt acctcggtct ccagttaacg    3420
ggcttggatg caagtgatgc gacgcagcgc gccctcattt gggcccccccg gccctgagcg   3480 gcctttcgtg gcagttgggt caaccggttg ggcgcgtgg agagtgtgtg ggatttgaag    3540
ggggtgtggg cggatcaagc tcagtccgac tcgcaaggat ctaccaccac cgcaacaagg   3600
aacgccttac cggagcaccc gaatgctttg gcctttcagg tgagtgtggt ggaagcgagt    3660
gcttacaagc caaacacgag ctccggccaa acccaatcca ctaacagttc cccctacctg    3720
cacttggtga agcctaagaa agttacccaa tccgacaagt tagacgacga tcttaaaaac    3780
ctgttggacc ccaaccaggt tcgcaccaag ctgcgccaaa gctttggtac agaccattcc    3840
acccagcccc agccccaatc gctcaaaaca acgacaccgg tatttgggac gagtagtggt    3900
aacctcagta gtgtgcttag tggtgggggt gctggagggg gttcttcagg ctcaggtcaa    3960
tctggcgtgg atctctcccc cgttgaaaaa gtgagtgggt ggcttgtggg gcagttacca    4020
agcacgagtg acggaaacac ctcctccacc aacaacctcg cgcctaatac taatacgggg    4080
aatgatgtgg tggggggttgg tcgactttct gaaagcaacg ccgcaaagat gaatgacgat   4140
gttgatggta ttgtacgcac cccactcgct gaactgttag atggggaagg acaaacagct   4200
gacactggtc cacaaagcgt gaagttcaag tctcctgacc aaattgactt caaccgcttg    4260
tttacccacc cagtcaccga tctgtttgat ccggtaacta tgttggtgta tgaccagtac    4320
ataccgctgt ttattgatat cccagcaagt gtgaaccccta aaatggttcg tttaaaggtc    4380
ttgagctttg acaccaacga acagagctta ggtctccgct tagagttctt taaacctgat    4440
```

-continued

| | |
|---|---|
| caagatacccc aaccaaacaa caacgttcag gtcaatccga ataacggtga cttcttacca | 4500 |
| ctgttaacgg cctccagtca aggtccccaa accttgttta gtccgtttaa ccagtgacct | 4560 |
| gattacgtgt tgccgttagc gatcactgta cctattgttg tgattgtgct cagtgttacc | 4620 |
| ttaggacttg ccattggaat cccaatgcac aagaacaaac aggccttgaa ggctgggttt | 4680 |
| gcgctatcaa accaaaaggt tgatgtgttg accaaagcgg ttggtagtgt ctttaaggaa | 4740 |
| atcattaacc gcacaggtat cagtcaagcg ccaaaacgct tgaaacaaac cagtgcggct | 4800 |
| aaaccaggag caccccgccc accagtacca ccaaagccag gggctcctaa gccaccagtg | 4860 |
| caaccaccta aaaacccgc ttag | 4884 |

<210> SEQ ID NO 8
<211> LENGTH: 4905
<212> TYPE: DNA
<213> ORGANISM: Mycoplasma pneumoniae

<400> SEQUENCE: 8

| | |
|---|---|
| atgcaccaaa ccaaaaaaac tgccttgtcc aagtccactt ggattctcat cctcaccgcc | 60 |
| accgcctccc tcgcgacggg actcaccgta gtgggacact tcacaagtac caccacgacg | 120 |
| ctcaagcgcc agcaatttag ctacacccgc cctgacgagg tcgcgctgcg ccacaccaat | 180 |
| gccatcaacc cgcgcttaac cccgtgaacg tatcgtaaca cgagcttttc ctccctcccc | 240 |
| ctcacgggtg aaaatcccgg ggcgtgggcc ttagtgcgcg acaacagcgc taagggcatc | 300 |
| actgccggca gtggcagtca acaaaccacg tatgatccca cccgaaccga agcggctttg | 360 |
| accgcatcaa ccacctttgc gttacgccgg tatgacctcg ccgggcgcgc cttatacgac | 420 |
| ctcgattttt cgaagttaaa cccgcaaacg cccacgcgcg accaaaacgg gcagatcacc | 480 |
| tttaacccct tggcggcttt tggtttgagt ggggctgcac cccaacagtg aaacgaggtc | 540 |
| aaaaacaagg tccccgtcga ggtggcgcaa gacccctcca atccttatcg gtttgccgtt | 600 |
| ttactcgtgc cgcgtagcgt ggtgtactat gagcagttgc agcgggggtt agcgctccct | 660 |
| aaccaaggga gttcgtcagg ctcagacagc actaaccaaa caggcgcaat gtttggcttg | 720 |
| aaggtgaagg atgcaaccgt ggatagttcg aagcaatcaa cggaaagctt aaagggcgaa | 780 |
| gaatcgagtt ccagttccac cacatcttcc acctccacca cccaacgtgg gggttcgtca | 840 |
| aatgaaaaca aagtcaaggc gttgcaggtg gcggtgaaaa agaaatccgg gagtcagggc | 900 |
| aactccggtg accaaggcac cgaacaggtg gaacttgaat ctaatgattt agccaacgcc | 960 |
| ccgattaaac ggggctccaa taacaaccag caagtccaac tcaaggcgga cgattttggt | 1020 |
| actgcccctt ccagttcggg atcaggcacc caagatggca cccccacccc ctgaacgccg | 1080 |
| tggttaacga ctgagcaaat tcacaacgac cccgccaaat tcgccgcctc gatcctgatt | 1140 |
| ctgtacgatg cgccttatgc gcgcaaccgt accgccattg accgcgttga tcacttggat | 1200 |
| cccaaggcca tgaccgcgaa ctatccgccc agttgaagaa cgcccaagtg aaaccaccac | 1260 |
| ggtttgtggg actgaaaggc gcgcgatgtt ttgctccaaa ccaccgggtt cttcaacccg | 1320 |
| cgccgccacc ccgagtggtt tgatggcggg cagacggtcg cggataacga aaagaccggg | 1380 |
| tttgatgtgg ataactctga aaacaccaag cagggctttc aaaaggaagc tgactccgac | 1440 |
| aagtcggccc cgatcgccct cccgtttgaa gcgtacttcg ccaacattgg caacctcacc | 1500 |
| tggttcgggc aagcgctttt ggtgtttggt ggcaatggcc atgttaccaa gtcggcccac | 1560 |
| accgcgccct tgagtatagg tgtctttagg gtgcgctata atgcaactgg taccagtgct | 1620 |
| actgtaactg gttgaccata tgccttactg ttctcaggca tggtcaacaa acaaactgac | 1680 |

```
gggttaaaga atctaccctt taacaataac cgctggtttg aatatgtacc acggatggca   1740
gttgctggcg ctaagttcgt tggtagggaa ctcgttttag cgggtaccat taccatgggt   1800
gataccgcta ccgtacctcg cttactgtac gatgaacttg aaagcaacct gaacttagta   1860
gcgcaaggcc aaggtctttt acgcgaagac ttgcaactct tcacaccta cggatgagcc    1920 aatcgtccgg atttaccaat cggggcttga agtagtagta gtagtagtca caacgcaccc   1980
tactacttcc acaataaccc cgattgacaa gaccgtccaa tccaaagtgt ggttgatgcc   2040
tttattaagc cctgagagga caagaacggt aaggatgatg ccaaatacat ctacccttac   2100
cgttacagtg gcatgtgagc ttgacaggta tacaactggt ccaataagct cactgaccaa   2160
ccattaagtg ctgactttgt caatgagaat gcttaccaac caaactcctt gtttgctgct   2220
attctcaatc cggaattgtt agcagctctt cccgacaagg ttaaatacgg taaggaaaac   2280
gagtttgctg ctaacgagta cgagcgcttt aaccagaagt taacggtagc tcctacccaa   2340
ggaacaaact gatcccactt ctcccccacg ctttcccgtt tctccaccgg gttcaacctt   2400 gtgggtcgg tgctcgacca ggtgttggat tatgtgccct ggattgggaa tgggtacagg    2460
tatggcaata accaccgggg cgtggatgat ataaccgcgc ctcaaaccag cgcggggtcg   2520
tccagcggaa ttagtacgaa cacaagtggt tcgcgttcct ctctcccgac gttttccaac   2580
atcggcgtcg gcctcaaagc gaatgtccaa gccaccctcg ggggcagtca gacgatgatt   2640
acaggcggtt cgcctcgaag aaccctcgac caagccaacc tccagctctg aacgggggcg   2700
gggtgaagga atgataaggc ttcaagtgga caaagtgacg accacaccaa gttcacgagc   2760
gctacgggga tgggccagca ggaacaatca ggtacctccg cggggaatcc cgactcgtta   2820
aagcaggata agattagtaa gagtggggat agtttaacca cgcaggacgg caatgcgatg   2880
gatcaacaag aggccaccaa ctacaccaac ctccccccca acctcacccc caccgctgat   2940
tgaccgaacg cgctgtcatt caccaacaag aacaacgcgc agcgcgccca gctgttcctg   3000
cgcggcctgt tgggcagcat cccggtgttg gttaataagt ccggccaaga tgataacagt   3060
aagtttaagg cggaggacca aaaatggtcc tacaccgact tacagtcgga ccaaaccaaa   3120
ctgaacctcc ccgcttacgg tgaggtgaat gggttgttga atccggcgtt ggtggaaacc   3180
tattttggga acacgcgagc gagtggttcg gggtccaaca cgaccagttc acccggtatc   3240
ggttttaaaa ttcccgaaca aagtggcaca acacaacgt cgaaggctgt gctgatcacc    3300
cccgggttgg cttgaacgcc gcaagacgtt ggtaacctcg ttgtcagtgg caccagcttc   3360
agcttccagc tcggcgggtg gttagttacg ttcacggact ttatcaaacc ccgcgctggt   3420
tacctcgggc tccagttaac gggcttggat gcaagtgatg cgacgcagcg cgctctcatt   3480 tgggccccc ggcctgagc ggcctttcgt ggcagtggg tcaacggtt gggccgcgtg       3540 gagagtgtgt gggatttgaa ggggtgtgg gcggatcaag ctcagtccga ctcgcaagga    3600
tctaccacca ccgcaacaag ggacgcctta ccggagcacc cgaatgcttt ggcctttcag   3660
gtgagtgtgg tggaagcgag tgcttacaag ccaaacacga gctccggcca aacccaatcc   3720
actaacagtt cccctacct gcacttggtg aagcctaaga agttatccaa atccgacaag    3780
ttagacgacg atcttaaaaa cctgttggac cccaaccagg ttcgcaccaa gctgcgccaa   3840
agctttggta cagaccattc cacccagccc cagccccaat cgctcaaaac aacgacaccg   3900
gtatttggga cgagtagtgg taacctcagt agtgtgctta gtggtggggg tgctggaggg   3960
ggttcttcag gctcaggtca atctggcgtg gatctctccc ccgttgaaaa agtgagtggg   4020
```

```
                                                           -continued
tggcttgtgg ggcagttacc aagcacgagt gacggaaaca cctcctccac caacaacctc     4080
gcgcctaata ctaatacggg gaatgatgtg gtggggttg gtcgactttc tgaaagcaac      4140
gccgcaaaga tgaacgacga tgttgatggt attgtacgca ccccactcgc tgaactgtta     4200
gatggggaag gacaaacagc tgacactggt ccacaaagcg tgaagttcaa gtctcctgac     4260
caaattgact tcaaccgctt gtttacccac ccagtcaccg atctgtttga tccggtaact     4320
atgttggtgt atgaccagta cataccgctg tttattgata tcccagcaag tgtgaaccct     4380
aaaatggttc gtttaaaggt cttgagcttt gacaccaacg aacagagctt aggtctccgc     4440
ttagagttct ttaaacctga tcaagatacc caaccaaaca acaacgttca ggtcaatccg     4500
aataacggtg acttcttacc actgttaacg gcctccagtc aaggtcccca aaccttgttt     4560
agtccgttta accagtgacc tgattacgtg ttgccgttag cgatcactgt acctattgtt     4620
gtgattgtgc tcagtgttac cttaggactt gccattggaa tcccaatgca caagaacaaa     4680
caggccttga aggctgggtt tgcgctatca aaccaaaagg ttgatgtgtt gaccaaagcg     4740
gttggtagtg tctttaagga aatcattaac cgcacaggta tcagtcaagc gccaaaacgc     4800
ttgaaacaaa ccagtgcggc taaaccagga gcaccccgcc caccagtacc accaaagcca     4860
ggggctccta agccaccagt gcaaccacct aaaaaacccg cttag                    4905
```

| | ************************************************************ | |

METHOD FOR DETECTING MICROORGANISMS BELONGING TO *MYCOPLASMA PNEUMONIAE* AND/OR *MYCOPLASMA GENITALIUM*

CROSS-REFERENCE TO RELATED APPLICATIONS

The present application is a 371 National Phase application of PCT/JP2010/071652, which application was filed Dec. 3, 2010, and which application claims priority to JP 2009-276115, filed Dec. 4, 2009 and JP 2010-023102, filed Feb. 4, 2010, all of the disclosures are hereby incorporated by reference in their entireties for all purposes.

TECHNICAL FIELD

The present invention relates to a method and a reagent kit for detecting microorganisms belonging to *Mycoplasma pneumoniae* which is, in general, a pathogenic microorganism for pneumonia, and/or *Mycoplasma genitalium*, using a molecule specific to the detection of the microorganisms as an indicator.

BACKGROUND ART (1) Patient Ratio and Symptoms of *Mycoplasma pneumoniae* Pneumonia

*Mycoplasma pneumoniae* infections are classified as a community-acquired atypical pneumonia, and it is said that the proportion of *Mycoplasma pneumoniae* infections in community-acquired pneumonia amounts to 30 to 40% in adults and to even 60 to 70% when the adults are limited to young adults aged 15 to 25. The infection route of *Mycoplasma pneumoniae* is a respiratory tract infection, and it is not rare that such infections spread in facilities such as schools, and in families. In addition, in the *Mycoplasma pneumoniae* infections, pneumonia occurs in about 3 to 5% of the infections, and the remainder is bronchitis, upper respiratory tract inflammation, or inapparent infection. Characteristic symptoms include an obstinate cough that is not accompanied by expectoration from an early period of infection, and may be sometimes accompanied by symptoms such as fever, headache, pharyngeal pain, chills, or general malaise.

(2) Current Status of Screening for *Mycoplasma pneumoniae* infections

A screening test of the culture from a pharyngeal swab sample in patients and an antibody screening test using a patient's serum are common as screening tests for *Mycoplasma pneumoniae* infections. Since *Mycoplasma pneumoniae* per se grows only in a special culture medium, the culturing is difficult to execute, and it is necessary to perform a PCR test for the final identification of *Mycoplasma pneumoniae*, the culture screening can be carried out only in limited facilities, and this is a current status of the screening test of the culture. In addition, a screening test to quickly obtain the results has been demanded, because several weeks are needed for the culture.

On the other hand, because the antibody screening test is generally easy in the procedure and provides results more quickly compared to the screening test of the culture, such an antibody screening test is a test that has been well used. But there are problems such that it is difficult to determine whether the infection is a previous one or a current one because IgM antibody titers of *Mycoplasma* are long-lasting, and it takes a long time to increase the antibody titers. In order to solve the above problems, the judgment based on rise in the antibody titers between the acute phase of the infection and the convalescent phase of the infection over time is recommended, but since it takes a very long time to perform an antibody testing until the convalescent phase, therapy is delayed, so that its delay may cause prolongation and worsening of symptoms, as well as may cause the adverse effect of infection expansion due to secondary infection.

In addition, in order to solve the above problems, antibodies and detection methods for specifically detecting a microorganism belonging to *Mycoplasma pneumoniae*, which are useful for diagnosing *Mycoplasma pneumoniae* infections, have been disclosed.

For example, patent literature 1 describes an immunodetection method using a monoclonal antibody against a membrane protein antigen of *Mycoplasma pneumoniae* of about 43 kilodaltons (kDa). Also, patent literature 2 describes that detection of *Mycoplasma pneumoniae* can be performed with high accuracy by using an antibody against ribosomal protein L7/L12. In addition, patent literature 3 describes that a quick and specific diagnosis of *Mycoplasma pneumoniae* infection is possible by using a monoclonal antibody against protein P1 of *Mycoplasma pneumoniae*, the monoclonal antibody having a cross-reactivity of only 1% or less to other species of the genus *Mycoplasma* or other pathogenic species of coexisting flora.

However, in order to detect a microorganism belonging to *Mycoplasma pneumoniae* in clinical specimens, the antibody described above and the detection method using the antibody may require a complicated pretreatment of the specimens containing the microorganism, and have a problem such that they are insufficient for a specific diagnosis of *Mycoplasma pneumoniae* because of still low specificity and sensitivity.

(3) *Mycoplasma genitalium* and Diseases

*Chlamydia trachomatis* is known as the major causative bacteria of nongonococcal urethritis. However, *Chlamydia trachomatis* is detected in about 30 to 40% of patients with nongonococcal urethritis, and, in most cases, it is not clear where their symptoms originate. In addition to *Chlamydia trachomatis*, microorganisms of the genera *Mycoplasma* and *Ureaplasma* have attracted attention, and *Mycoplasma genitalium* in particular is shown as one of the causative bacteria of nongonococcal urethritis and sexually transmitted disease.

(4) Current Status of Screening for *Mycoplasma genitalium* Infections

Reports of *Mycoplasma genitalium* infections by the culture method or the PCR method have been published in papers, but since a quick diagnosis cannot be performed by these methods, a method for detecting quickly and specifically a microorganism belonging to *Mycoplasma genitalium* in clinical specimens has been demanded.

CITATION LIST

Patent Literature

[Patent literature 1] Japanese Unexamined Patent Publication (Kokai) No. 63-298
[Patent literature 2] WO2001/057199
[Patent literature 3] Japanese Unexamined Patent Publication (Kokai) No. 5-304990

SUMMARY OF INVENTION

Technical Problem

According to conventional methods, microorganisms belonging to *Mycoplasma pneumoniae* and/or *Mycoplasma*

*genitalium* could not be quickly and specifically detected. Therefore, since it is not possible to quickly diagnose the infections from *Mycoplasma pneumoniae* and/or *Mycoplasma genitalium*, therapy is delayed, and its delay may cause prolongation and worsening of symptoms, as well as the adverse effect of infection expansion due to secondary infection. This is the current situation. If infections with these *Mycoplasmas* can be quickly detected/diagnosed, it becomes possible to administer a macrolide antibiotic effective for the *Mycoplasmas* and start the correct treatment in the early infection stage.

Further, *Mycoplasma pneumoniae* and *Mycoplasma genitalium* are known to be serologically very close to each other, but since the infection site (such as tissues and organs) of *Mycoplasma pneumoniae* is different from that of *Mycoplasma genitalium* as mentioned above, if it is possible to identify a molecule capable of specifically detecting the two microorganisms, it was considered that diagnosis of both infectious diseases becomes possible using the molecule as an indicator.

The present invention has been made in view of the problems. The object of the present invention is to specify a molecule to rapidly and specifically diagnose the *Mycoplasma pneumoniae* and/or *Mycoplasma genitalium* infections, and to provide a detection method and a detection kit using the molecule as an indicator.

Solution to Problem

Under these circumstances, the present inventors have conducted intensive studies, and have found that DnaK of microorganisms belonging to *Mycoplasma pneumoniae* and/or *Mycoplasma genitalium* can be used as an indicator to rapidly and specifically detect *Mycoplasma pneumoniae* and/or *Mycoplasma genitalium* infections. The DnaK protein, which is also called Heat Shock Protein 70 (Hsp70), was found as a group of proteins the expression of which was increased when cells were exposed to stress conditions such as heat to protect the cells, and is currently known to participate in the intracellular transport or refolding (molecular chaperone function) of proteins translated. The advantages in using the DnaK protein as an index in immunological analysis methods reside in the facts that:
(1) the DnaK protein is always expressed, because it participates in the transport or refolding of proteins,
(2) DnaK accounts for approximately 1% of the total proteins, and
(3) DnaK is present, not as a monomer, but as a trimer, a hexamer, or further multimers.

The present invention has been achieved based on these findings.

The present invention provides as follows:
[1] A method for detecting *Mycoplasma pneumoniae* or *Mycoplasma genitalium*, characterized by using DnaK of *Mycoplasma pneumoniae* or *Mycoplasma genitalium* as an indicator.
[2] The method of [1], wherein a DnaK protein is immunologically analyzed.
[3] An anti-DnaK antibody specific to *Mycoplasma pneumoniae* or *Mycoplasma genitalium*.
[4] A kit for detecting *Mycoplasma pneumoniae* or *Mycoplasma Genitalium*, comprising the anti-DnaK antibody of [3].
[5] The method of [1], using a DnaK gene as an indicator.
[6] A primer or probe specific to *Mycoplasma pneumoniae* or *Mycoplasma genitalium*.
[7] A kit for detecting *Mycoplasma pneumoniae* or *Mycoplasma genitalium*, comprising the primer or probe of [6].

The term "the microorganisms" as used herein means *Mycoplasma pneumoniae* or *Mycoplasma genitalium*, in particular, microorganisms which have pathogenicity and are significant to be diagnosed as microorganisms causative of the diseases described below.

The term "antibody which specifically reacts with the microorganisms" as used herein means an antibody which specifically reacts with the species or the genus of the microorganisms. An antibody which specifically reacts with the species of the microorganisms is particularly useful in the diagnosis of microorganism infections.

Advantageous Effects of Invention

According to the method for detecting microorganisms belonging to *Mycoplasma pneumoniae* and/or *Mycoplasma genitalium* using the specific molecule in the present invention as an indicator, *Mycoplasma pneumoniae* and/or *Mycoplasma genitalium* infections caused by the microorganisms can be rapidly and specifically diagnosed.

BRIEF DESCRIPTION OF THE DRAWINGS

FIG. 1 illustrates a comparison of nucleotide sequences (1-720) of DnaK genes (SEQ ID NO: 6) in *Mycoplasma pneumoniae* strains M129 (P1 genotype: type I) and FH (P1 genotype: type II).

FIG. 2 illustrates, following FIG. 1, a comparison of nucleotide sequences (721-1440) of the DnaK genes in both *Mycoplasma pneumoniae* strains.

FIG. 3 illustrates, following FIG. 1 and FIG. 2, a comparison of nucleotide sequences (1441-1788) of the DnaK genes in both *Mycoplasma pneumoniae* strains.

FIG. 4 illustrates a comparison of nucleotide sequences (1-717 for M129 strain) of P1 genes (M129 strain: SEQ ID NO: 7, and FH strain: SEQ ID NO: 8) in *Mycoplasma pneumoniae* strains M129 (P1 genotype: type I) and FH (P1 genotype: type II).

FIG. 5 illustrates, following FIG. 4, a comparison of nucleotide sequences (718-1416 for M129 strain) of the P1 genes in both *Mycoplasma pneumoniae* strains.

FIG. 6 illustrates, following FIG. 4 and FIG. 5, a comparison of nucleotide sequences (1417-2136 for M129 strain) of the P1 genes in both *Mycoplasma pneumoniae* strains.

FIG. 7 illustrates, following FIG. 4 to FIG. 6, a comparison of nucleotide sequences (2137-2856 for M129 strain) of the P1 genes in both *Mycoplasma pneumoniae* strains.

FIG. 8 illustrates, following FIG. 4 to FIG. 7, a comparison of nucleotide sequences (2857-3564 for M129 strain) of the P1 genes in both *Mycoplasma pneumoniae* strains.

FIG. 9 illustrates, following FIG. 4 to FIG. 8, a comparison of nucleotide sequences (3565-4284 for M129 strain) of the P1 genes in both *Mycoplasma pneumoniae* strains.

FIG. 10 illustrates, following FIG. 4 to FIG. 9, a comparison of nucleotide sequences (4285-4884 for M129 strain) of the P1 genes in both *Mycoplasma pneumoniae* strains.

DESCRIPTION OF EMBODIMENTS

The present invention now will be further illustrated in detail by, but is by no means limited to, the following embodiments of the present invention as typical examples.

The method of the present invention for detecting *Mycoplasma pneumoniae* or *Mycoplasma genitalium* is characterized in that DnaK of the microorganisms is used as an indicator to detect *Mycoplasma pneumoniae* and/or *Mycoplasma genitalium* (i.e., either of *Mycoplasma pneumoniae* or *Mycoplasma genitalium*, or both *Mycoplasma pneumoniae* and *Mycoplasma genitalium*, most preferably, both *Mycoplasma pneumoniae* and *Mycoplasma genitalium*). *Mycoplasma pneumoniae* and/or *Mycoplasma genitalium* infections can be diagnosed by detecting these microorganisms.

The *Mycoplasma pneumoniae* infection which may be diagnosed by the present invention is mycoplasmal pneumonia. The *Mycoplasma genitalium* infection is non-gonococcal non-chlamydial urethritis or cervicitis.

In the diagnosis of the *Mycoplasma pneumoniae* infection, a sample in which *Mycoplasma pneumoniae* may exist may be used. Examples of the sample include pharyngeal swab, nasopharyngeal swab, nasal aspirate, nasal mucus, sputum, and bronchoalveolar lavage fluid. When the *Mycoplasma genitalium* infection is to be diagnosed, a sample in which *Mycoplasma genitalium* may exist may be used. Example of the sample include urine, urethral swab specimens, and cervical swab specimens. The identification of the two infections can be decided by the collection site of the sample as a target for measurement.

DnaK which is used as an indicator in the present invention is a DnaK protein (NCBI number: NP_110122) or a DnaK gene (NCBI number: NC_000912 REGION: 521837 . . . 523624) derived from *Mycoplasma pneumoniae*, or a DnaK protein (NCBI number: AAC71527) or a DnaK gene (NCBI number: L43967 REGION: 374919 . . . 376706) derived from *Mycoplasma genitalium*. The above-mentioned proteins and genes are examples of a strain belonging to the microorganisms, and the DnaK sequences of the microorganisms within the scope of the present invention include sequences corresponding to the DnaK proteins and genes described above.

As shown in Example 8 described below, the DnaK genes derived from different *Mycoplasma pneumoniae* strains absolutely (100%) accorded with each other, even among strains in which the types of the P1 gene of *Mycoplasma pneumoniae* were different, and no variations were detected among strains collected from various places and over the past 50 years. From this, it is considered that the sequences of the DnaK gene and the DnaK protein of *Mycoplasma pneumoniae* are stable. Therefore, it is preferable to refer to the nucleotide sequences or the amino acid sequences published by NCBI as described above.

1. Method and Kit for Detecting Microorganisms Using Antibody

The first embodiment of the method for detecting *Mycoplasma pneumoniae* or *Mycoplasma genitalium* of the present invention is characterized by using an anti-DnaK antibody specific to the microorganisms. When the specific antibody is selected, the specificity to the microorganisms is at least $10^5$ CFU/mL or higher, preferably $10^4$ CFU/mL or higher, and more preferably $10^3$ CFU/mL, and the specificity to the other microorganisms is at least $10^7$ CFU/mL or lower, and preferably $10^8$ CFU/mL or lower.

The antibody which may be used in the present invention may be a polyclonal antibody or a monoclonal antibody. These antibodies may be obtained by the following methods or other similar methods, but the method is not limited to the same.

As the first embodiment of the method for preparing the antibody, the complete length of the DnaK protein or its partial peptide may be used to prepare the antibody. With respect to microorganisms of which the nucleotide sequence and the amino acid sequence of the DnaK protein are known, a peptide fragment may be synthesized based on a region which shows less similarity to the amino acid sequences of DnaK proteins of other microorganisms. The length of the peptide for preparing the antibody is not limited, but in the case of the antibody against the DnaK protein, a peptide having a length capable of characterizing the protein, preferably 5 amino acids or more, and most preferably 8 amino acids or more, may be used. This peptide or the complete length of the protein alone, or a conjugate thereof crosslinked with a carrier protein such as KLH (keyhole-limpet hemocyanin) or BSA (bovine serum albumin), may be inoculated into an animal, optionally along with an adjuvant, and a serum is collected from the animal to obtain an antiserum containing an antibody (polyclonal antibody) which recognizes the DnaK protein. An antibody which is purified from the antiserum may be used. Examples of the animal which may be inoculated include a sheep, a horse, a goat, a rabbit, a mouse, and a rat, and a rabbit or a goat is preferable for preparing a polyclonal antibody. A monoclonal antibody may be obtained in accordance with a known method for preparing hybridoma cells, and a mouse is preferable in this case.

A fusion protein of the complete length or an amino acid sequence consisting of 5 residues or more (preferably 8 residues or more) of the protein with glutathione S-transferase or the like may be used as an antigen, after purification of the fusion protein, or without purification. The antibody may be also prepared by a genetically recombinant antibody expressed in culture cells using an immunoglobulin gene isolated by a gene cloning method and various methods described in the publication: Antibodies; A laboratory manual, E. Harlow et al., Cold Spring Harbor Laboratory Press.

From the antibodies prepared as described above, an antibody having a high specificity may be prepared by selecting an antibody which specifically reacts with *Mycoplasma pneumoniae* and/or *Mycoplasma genitalium* (i.e., either of *Mycoplasma pneumoniae* or *Mycoplasma genitalium*, or both *Mycoplasma pneumoniae* and *Mycoplasma genitalium*, most preferably, both *Mycoplasma pneumoniae* and *Mycoplasma genitalium*), and does not react with other pathogenic microorganisms, in accordance with a known method.

The antibody against the DnaK which may be used as the marker antigen of the present invention may be obtained by the following methods or other similar methods, but the method is not limited to the same.

a) With respect to microorganisms of which the nucleotide sequence and the amino acid sequence of the DnaK protein are known, a peptide fragment may be synthesized based on a region which shows less similarity to the amino acid sequences of DnaK proteins of other microorganisms, and a polyclonal or monoclonal antibody may be prepared using the peptide fragment as an antigen to obtain the antibody of interest.

The complete length of the nucleotide sequence of the gene may be obtained using common genetic engineering techniques, such as gene amplification by a PCR method using DNA sequences at both the termini of the known gene as primers, or hybridization using a homologous sequence as a template probe.

Next, a protein antigen of interest may be obtained by constructing a fusion gene with other protein genes, introducing the fusion gene into a host such as *E. coli* by a known gene introduction method, overexpressing the fusion protein, and purifying the expressed protein by an affinity column chromatography method using an antibody against the protein used for preparing the fusion protein. In this case, since the complete length of the DnaK protein becomes antigens, if an antibody against an amino acid region which is conserved between microorganisms outside the scope is obtained, such an antibody cannot be used in the present invention. Therefore, with respect to an antigen obtained by this method, the antibody of interest may be obtained by obtaining hybridomas producing monoclonal antibodies and selecting a clone producing an antibody which specifically reacts with the microorganisms.

b) With respect to microorganisms of which the amino acid sequence of the DnaK protein is unknown, since the amino acid sequences of the DnaK protein have a homology of 80-1000, preferably 90-100%, between different species, the protein gene of interest may be easily obtained using common genetic engineering techniques, such as gene amplification of a specific sequence region by a PCR method based on a sequence homologous to the amino acid sequence, or hybridization using a homologous sequence as a template probe.

The protein antigen of interest may be obtained by constructing a fusion gene of the protein gene with other protein genes, introducing the fusion gene into a host such as *E. coli* by a known gene introduction method, overexpressing the fusion protein, and purifying the expressed protein by an affinity column method using an antibody against the protein used for preparing the fusion protein. In this case, since the complete length of the DnaK protein becomes antigens, if an antibody against an amino acid region which is conserved between microorganisms outside the scope is obtained, such an antibody cannot be used in the present invention. Therefore, with respect to an antigen obtained by this method, the antibody of interest may be obtained by obtaining hybridomas producing monoclonal antibodies and selecting a clone producing an antibody which specifically reacts with the microorganisms.

c) As another method in the case that the amino acid sequence of the DnaK protein is unknown, a synthetic peptide consisting of 5-30 amino acids corresponding to a common sequence region which are conserved between microorganisms in known amino acid sequences of the DnaK protein is prepared, and a polyclonal or monoclonal antibody is prepared using the peptide sequence in accordance with a known method. A highly purified DnaK protein may be obtained by purifying a cell homogenate of a microorganism of interest by affinity column chromatography using the antibody. When the purity of the protein is not sufficient, the purity may be improved by a known purification method, such as ion-exchange chromatography, hydrophobic chromatography, or gel filtration. The antibody of interest may be obtained by obtaining hybridomas using the obtained purified DnaK protein antibody, and selecting a hybridoma producing an antibody which specifically reacts with the microorganisms.

As the second embodiment of the method for preparing the antibody, *Mycoplasma pneumoniae* may be used as an antigen to prepare an antibody which reacts with the DnaK protein and is specific to *Mycoplasma pneumoniae* and/or *Mycoplasma genitalium*, as shown in Example 1.

Similarly, *Mycoplasma genitalium* may be used as an antigen to prepare the antibody. In the case that the microorganism is used as an antigen, the antigen may be prepared in accordance with a known method. Examples of the method include sonication, heat treatment, surfactant treatment, formalin treatment, freezing and thawing treatment, and treatment with hydrochloric acid.

The antibody of the present invention which is obtained by the methods described above and is specific to the microorganisms may be used in various immunological assays, and various detection reagents and kits specific to the microorganisms of interest may be provided.

The antibody may be used in any of the known immunological assays, for example, an agglutination method using polystyrene latex particles onto which the antibody is bound, an ELISA method carried out in a microtiter plate, immunochromatography, or a sandwich method using the antibody labeled with colored particles, particles capable of developing a color, magnetic particles, an enzyme, or a fluorescent substance, alone or as a combination.

In the detection method using DnaK as an indicator of the present invention, *Mycoplasma pneumoniae* and/or *Mycoplasma genitalium* may be specifically detected without intentionally disrupting the cells, or a known method for treating microorganisms may be used to carry out detection with high sensitivity. More particularly, a treatment method using an extraction reagent comprising various surfactants such as Triton X-100, Tween-20, or SDS, an enzyme treatment method using an appropriate enzyme such as a protease, or a known method for disrupting a cell structure, such as a disruption of microorganism cells by a physical method, may be used. It is preferable that optimum conditions for extraction are selected for each microorganism by examining the combination of reagents such as surfactants.

The reagent kit for detecting the microorganism using the antibody of the present invention corresponds to the reagent kit for detection using the detection method.

The kit is not limited, so long as it contains at least one antibody of the present invention. The number, type, and combination of the antibodies used may be appropriately changed in accordance with the immunological assay to be used. The kit may contain a liquid for pretreatment in the extraction method described above, as a pretreatment of a sample.

2. Method and Kit for Detecting Microorganisms Using Gene

As a method for extracting DNA, a known method may be used. Examples of the method include a solubilization of a sample with a surfactant, or deproteinization using a deproteinization agent, to obtain DNA. Preferably, so long as the DnaK gene as described below may be analyzed, for example, when the gene extracted is next amplified by a PCR method, the DNA preferably contains no inhibitors of PCR reaction.

As a method for pretreating a sample, a similar approach as described in the method for detecting the microorganisms using an antibody may be used.

The amount of DNA extracted is not limited so long as an amount capable of analyzing the DnaK gene is extracted. When the DNA is subjected to a PCR method, the amount is, for example, 5 to 50 fg or more per reaction.

The DNA extracted is used to analyze the DnaK gene. The analysis of the DnaK gene may be carried out in accordance with a known method. Examples of the method include a method for detecting the amplification of the DnaK gene by a PCR method, and a method for specifying the DnaK gene by a probe method. For example, any method for amplifying the DnaK gene by a PCR method may be used, so long as the nucleotide sequence of interest may be amplified. Any method for specifying the DnaK gene by a probe method may be used, so long as the nucleotide sequence of interest may be specified.

To amplify or specify the desired nucleotide sequence of the DnaK gene, a sequence having an 80-100% homology with respect to *Mycoplasma pneumoniae* and/or *Mycoplasma genitalium* and having a homology of preferably 60% or less with respect to other pathogenic microorganisms may be appropriately selected. The primer or probe may contain one or more variations, deletions, or additions in its nucleotide sequence, so long as the DNA fragment of interest may be amplified.

For example, when the DnaK gene of *Mycoplasma pneumoniae* is to be amplified, PCR amplification primers may be designed on the basis of the DnaK gene sequence of *Mycoplasma pneumoniae* (NCBI number: NC_000912 REGION: 521837 . . . 523624) published in NCBI, as described in the Examples below. More particularly, sense primer MpDnaK_S and antisense primer MpDnaK_A may be used to amplify the complete length of the DnaK gene.

When the DnaK gene of *Mycoplasma genitalium* is to be amplified, PCR amplification primers may be designed on the basis of the DnaK gene sequence of *Mycoplasma genitalium* (NCBI number: L43967 REGION: 374919 . . . 376706) published in NCBI.

As shown in Example 8, the DnaK genes derived from different *Mycoplasma pneumoniae* strains absolutely (100%) accorded with each other, even among strains in which the types of the P1 gene of *Mycoplasma pneumoniae* were different, and no variations were detected among strains collected from various places and over the past 50 years. From this, it is not necessary to take into consideration the difference between *Mycoplasma pneumoniae* strains in order to specifically detect the DnaK gene of *Mycoplasma pneumoniae*, and the primers or probe may be designed by taking into consideration the differences among the strains other than *Mycoplasma pneumoniae*.

Further, because it is considered that the sequence of the DnaK protein of *Mycoplasma pneumoniae* is also conservative, antibodies prepared using the DnaK protein are considered to show no difference in reactivity with respect to the genotype, the place for collection, and the time of collection, and thus, may be used over a wide area and time.

The reagent kit for detecting the microorganisms using the gene of the present invention corresponds to the reagent kit for detection using the detection method. This is a kit which is used for the method for specifically detecting *Mycoplasma pneumoniae* and/or *Mycoplasma genitalium* and which is characterized by comprising at least two types of primers for amplifying a nucleotide sequence specific to the DnaK gene of interest.

As another embodiment, the kit is characterized by comprising at least one type of probe for specifying a nucleotide sequence specific to the DnaK gene of interest.

These kits may further contain a liquid for pretreatment in the extraction method described above, as a pretreatment of a sample.

EXAMPLES

The present invention now will be further illustrated by, but is by no means limited to, the following Examples.

Example 1

Preparation of Antibodies Specific to *Mycoplasma pneumoniae* and *Mycoplasma genitalium* and Identification of a Specific Antigen (1) Preparation of Monoclonal Antibodies Specific to *Mycoplasma pneumoniae* and *Mycoplasma genitalium*
(1-1) Cultivation of Strains for Immunization and Preparation of Immunogens PPLO glucose broths (containing horse serum, fresh yeast extract, and thallium acetate) were each separately inoculated with one of 6 strains of *Mycoplasma pneumoniae* (FH, Bru, Mac, M52, PI1428, and M129-B7 strains: purchased from ATCC), and cultivation was carried out at 37° C. for 7 days under aerobic conditions. Each strain collected by centrifugation was washed and suspended in PBS. These suspensions were frozen and thawed to prepare immunogens.

(1-2) Immunization

Six-week-old female Balb/c mice (CREA Japan, Inc.) were used for immunization. Each immunogen solution derived from a strain was emulsified with Freund's complete adjuvant (SIGMA). Each emulsion (100 μg of antigen) was subcutaneously injected into a mouse. Until an increase in antibody titer against immunogen was observed in each mouse, 50 μg of each antigen emulsified with Freund's incomplete adjuvant (SIGMA) was subcutaneously injected into the mouse every two weeks. Further, 25 μg of each antigen diluted with PBS was intraperitoneally injected into the mouse three days before cell fusion.

(1-3) Preparation of Hybridomas

The following procedures were carried out in accordance with a conventional method. Spleen cells aseptically collected from immunized mice were fused with myeloma cells (P3U1) using polyethylene glycol 1500 (Roche), and inoculated into wells of 96-well plates. Hybridoma cells were selectively cultivated using a HAT medium, and their culture supernatants were screened under the following ELISA conditions. Immobilization for ELISA was carried out using *Mycoplasma pneumoniae* antigen (1 μg/mL) derived from each of the 6 strains used as immunogens. After a blocking treatment for wells, each culture supernatant was added to the wells and incubated at 4° C. overnight. The wells were washed with a washing liquid three times, and a 2000-fold diluted HRP-labeled rabbit anti-mouse Ig antibody (Dako) was added to the wells and incubated at room temperature for 1 hour. The wells were washed with a washing liquid three times, and a substrate (TMBZ) solution was added to the wells and incubated at room temperature for 10 minutes. After the reaction was stopped, an absorbance at 450 nm was measured. The selected hybridomas were further screened by a limiting dilution method to establish clone strains. With respect to monoclonal antibodies produced from 16 strains in the established clone strains, the following experiments were carried out. The monoclonal antibodies produced from the 16 clone strains reacted with all the immunogens derived from the 6 strains.

(1-4) Determination of Molecular Weight of Proteins Recognized by Monoclonal Antibodies The molecular weight of each protein recognized by the 16 monoclonal antibodies was determined by Western blotting. First, 10 μg of *Mycoplasma pneumoniae* antigen (FH strain) was electrophoresed by SDS-PAGE and blotted onto nitrocellulose membranes. Each culture supernatant of the 16 clones was added to the membranes and incubated at room temperature for 1 hour. The membranes were washed with a washing liquid three times, and a 1000-fold diluted HRP-labeled rabbit anti-mouse Ig antibody was added to the membranes and incubated at room temperature for 1 hour. The membranes were washed with a washing liquid three times, and a substrate (4-chloro-1-naphthol) solution was added to the membranes and incubated at room temperature for 10 minutes. After the development, the membranes were washed with a distilled water to stop the reaction.

As a result, it was found that 10 monoclonal antibodies recognized a molecule having a molecular weight of 62-69 kDa and 6 monoclonal antibodies recognized a molecule having a molecular weight of 40-45 kDa. From this result, we attempted to identify the antigen with respect to the molecule of 62-69 kDa which was considered to have a high immunogenicity because many clones were obtained.

(1-5) Identification of Subclass of Obtained Antibodies

Iso Strip (Roche) was used to determine the subclass of 10 monoclonal antibodies which recognized the molecule of 62-69 kDa. It was found that 6 antibodies were H chain G1/L chain κ, 1 antibody was H chain G1/L chain λ, 1 antibody was H chain 2b/L chain κ, 1 antibody was H chain 2b/L chain λ, and 1 antibody was H chain 2a/L chain λ.

(2) Identification of Antigen Specific to *Mycoplasma pneumoniae* and *Mycoplasma genitalium*

(2-1) Purification of Antigen Recognized by Monoclonal Antibodies (2-1-1) Cultivation of Strain A *Mycoplasma pneumoniae* M129-B7 strain, of which the entire gene sequence had been already determined, was used to purify an antigen. *Mycoplasma pneumoniae* (M129-B7 strain) was inoculated into a PPLO glucose broth (containing horse serum, fresh yeast extract, and thallium acetate), and cultivated at 37° C. for 7 days under aerobic conditions. The strain collected by centrifugation was washed and suspended in PBS. The suspension was frozen.

(2-1-2) Purification of Recognized Antigen by Affinity Chromatography

The monoclonal antibody MCM12 obtained in (1) was bound to CNBr-activated Sepharose 4B (GE healthcare) as a column carrier to prepare an affinity column for antigen purification. The binding to the column carrier was carried out by reacting IgG 5 mg/mL gel in 0.1 mol/L NaHCO$_3$—NaOH and 0.5 mol/L NaCl (pH 8.3) at 4° C. overnight. Unreacted groups were blocked using a 0.2 mol/L glycine buffer (pH 8).

Proteins extracted from the *Mycoplasma pneumoniae* strain were applied to the column. After a non-adsorbed fraction was eluted, a column-adsorbed fraction was eluted using 3 mol/L sodium thiocyanate and collected. This fraction was dialyzed against 50 mmol/L PBS (pH 7) to obtain a purified product.

(2-2) Identification of Protein Recognized by Obtained Monoclonal Antibodies (2-2-1) Determination of Molecular Weight of Recognized Protein by SDS-Page The purified antigen was analyzed by SDS-PAGE and Western blotting. The purified antigen (0.1 µg) was electrophoresed by SDS-PAGE and blotted onto nitrocellulose membranes. Monoclonal antibody MCM12 or monoclonal antibody MCM19 (10 µg/mL IgG solution) was separately added to the membranes and incubated at room temperature for 1 hour. The membranes were washed with a washing liquid three times, and a 1000-fold diluted HRP-labeled rabbit anti-mouse Ig antibody was added to the membranes and incubated at room temperature for 1 hour. The membranes were washed with a washing liquid three times, and a substrate (4-chloro-1-naphthol) solution was added to the membranes and incubated at room temperature. After the development, the membranes were washed with a distilled water to stop the reaction.

It was confirmed that both antibodies recognized the purified antigen.

(2-2-2) Analysis of N-Terminal Amino Acid Sequence of Purified Antigen

The N-terminal 10 amino acid residues of the purified antigen protein were analyzed in accordance with a conventional method. The purified antigen was electrophoresed by SDS-PAGE. A PVDF membrane on which the sample was blotted was washed with 50% methanol/0.1% trifluoroacetic acid and methanol and dried, and 10 cycles of amino acid sequencing was carried out from the N-terminus. A protein sequencer PPSQ-23A (Shimadzu) and a PTH analyzer SPD-10A (Shimadzu) were used as analyzers.

As a result, the following sequence was obtained:

```
        S T D N G L I I G I         (SEQ ID NO: 1)
```

A search was carried out using the database Swiss-Prot in accordance with a conventional method, and the obtained sequence completely accorded with the sequence consisting of the 2nd to 11th amino acid residues of chaperone protein DnaK of *Mycoplasma pneumoniae*. The molecular weight of the DnaK deduced from its amino acid sequence was 65 kDa, which nearly accorded with the molecular weight of the antibody-recognized antigen determined by Western blotting.

As described above, it was confirmed that the antibodies obtained above were anti-DnaK antibodies specific to *Mycoplasma pneumoniae* and *Mycoplasma genitalium*.

Example 2

Examination of Sensitivity and Cross-Reactivity Of Obtained Antibodies by ELISA Method In the monoclonal antibodies obtained in Example 1, monoclonal antibody MCM12 and monoclonal antibody MCM19 were used to examine the sensitivity and cross-reactivity of the antibodies.

(1) Cultivation and Preparation of Strains to be Examined (1-1) Strains For Sensitivity Test PPLO glucose broths (containing horse serum, fresh yeast extract, and thallium acetate) were each separately inoculated with one of the 8 strains of *Mycoplasma pneumoniae* shown in Table 1, and cultivation was carried out at 37° C. for 4 days under aerobic conditions. Strains in which the broth reached pH 6.8 were used as test strains. To determine the number of each strain in the broth, 10-step dilution series were prepared with sterilized PBS, and 10 µL of each dilution was inoculated onto PPLO (containing horse serum, fresh yeast extract, and thallium acetate) agar media and incubated at 37° C. for 10 days. Growth colonies on the agar media were counted under an optical microscope having a magnification of 40 to calculate the colony forming unit of each strain.

TABLE 1

| Strain | ATCC No. |
| --- | --- |
| *Mycoplasma pneumoniae* FH | 15531 |
| *Mycoplasma pneumoniae* Bru | 15377 |
| *Mycoplasma pneumoniae* Mutant 22 | 39505 |
| *Mycoplasma pneumoniae* Mac | 15492 |
| *Mycoplasma pneumoniae* M52 | 15293 |
| *Mycoplasma pneumoniae* PI1428 | 29085 |
| *Mycoplasma pneumoniae* M129-B7 | 29342 |
| *Mycoplasma pneumoniae* UTMB-10P | 49894 |

(1-2) Strains for Cross-Reactivity Test-1

Strains belonging to the genus *Mycoplasma* other than *Mycoplasma pneumoniae* shown in (1-1), the genus *Ureaplasma*, and the genus *Acholeplasma* were cultivated in accordance with the broths and the culture conditions shown in Table 2. The cultivation was carried out at 37° C. The terms "aerobic" and "anaerobic" in Table 2 mean aerobic cultivation and anaerobic cultivation, respectively. To determine the number of each strain in the broth, 10-step dilution series were prepared with sterilized PBS, and 10 µL of each dilution was inoculated onto PPLO (containing horse serum, fresh yeast extract, and thallium acetate) agar and incubated at 37° C. for 10 days. Growth colonies on the agar were counted under an optical microscope having a magnification of 40 to calculate the colony forming unit of each strain. The test was carried out at a number of $10^6$ to $10^7$ cfu/mL.

TABLE 2

| Strain | ATCC No. | Medium | Conditions |
|---|---|---|---|
| Mycoplasma genitalium | 33530 | PPLO glucose broth (thallium⁻) | 4 days, aerobic |
| Mycoplasma fermentans | 19989 | PPLO glucose broth | 4 days, aerobic |
| Acholeplasma laidlawii | 23206 | PPLO glucose broth | 4 days, aerobic |
| Acholeplasma oculi | 51735 | PPLO glucose broth | 4 days, aerobic |
| Mycoplasma penetrans | 55252 | PPLO glucose broth | 4 days, aerobic |
| Mycoplasma pirum | 25960 | PPLO glucose broth | 4 days, aerobic |
| Mycoplasma hominis | 23114 | PPLO arginine broth (thallium⁻) | 3 days, aerobic |
| Mycoplasma orale | 23714 | PPLO arginine broth | 3 days, aerobic |
| Mycoplasma salivarium | 23064 | PPLO arginine broth | 3 days, aerobic |
| Mycoplasma arthritidis | 19611 | PPLO arginine broth | 3 days, aerobic |
| Mycoplasma buccale | 23636 | PPLO arginine broth | 3 days, aerobic |
| Mycoplasma faucium | 25293 | PPLO arginine broth | 3 days, anaerobic |
| Mycoplasma lipophilum | 27104 | PPLO arginine broth | 3 days, aerobic |
| Mycoplasma primatum | 25948 | PPLO arginine broth | 3 days, aerobic |
| Mycoplasma spermatophilum | 49695 | PPLO arginine broth | 3 days, anaerobic |
| Ureaplasma parvum | 700970 | T-broth | 2 days, aerobic |
| Ureaplasma urealyticum | 27618 | T-broth | 2 days, aerobic |

(1-3) Strains for Cross-Reactivity Test-2

Table 3 to Table 6 show microorganisms which were used in a cross-reactivity test of bacteria and fungi other than the genus *Mycoplasma*, the genus *Ureaplasma*, and the genus *Acholeplasma* used in (1-1) and (1-2), and the culture conditions. Heart infusion agar (Difco), trypticase soy agarII with 5% sheep blood (Becton, Dickinson and Company), chocolate agar (NISSUI), modified GAM agar (NISSUI), skirrows medium (Becton, Dickinson and Company), and Sabouraud-dextrose agar (Difco) were used as media.

These strains were cultivated on agar, and suspended in sterilized PBS at a concentration of $10^7$ to $10^8$ cfu/mL to prepare test strains. To determine the number of each strain, each test suspension in which each strain was suspended in sterilized PBS was stepwisely (10-step) diluted with the same PBS, and 50 μL of each dilution was inoculated onto agar media. Growth colonies on the media were counted by the naked eye.

The blank spaces in the "Strain No." column of the tables mean strains which were isolated and identified from clinical specimens.

TABLE 3

| Strain | Strain No. | Medium | Conditions |
|---|---|---|---|
| Branhamella catarrhalis | | Heart infusion agar | 37° C., 18 hours, aerobic |
| Citrobacter freundii | ATCC 8090 | Heart infusion agar | 37° C., 18 hours, aerobic |
| Enterobacter cloacae | ATCC 13047 | Heart infusion agar | 37° C., 18 hours, aerobic |
| Escherichia coli | ATCC 25932 | Heart infusion agar | 37° C., 18 hours, aerobic |
| Escherichia hermannii | ATCC 33650 | Heart infusion agar | 37° C., 18 hours, aerobic |
| Klebsiella pneumoniae | ATCC 27736 | Heart infusion agar | 37° C., 18 hours, aerobic |
| Leclercia adecarboxylata | | Heart infusion agar | 37° C., 18 hours, aerobic |
| Proteus mirabilis | ATCC29906 | Heart infusion agar | 37° C., 18 hours, aerobic |
| Proteus vulgaris | ATCC 6380 | Heart infusion agar | 37° C., 18 hours, aerobic |
| Pseudomonas aeruginosa | ATCC 27853 | Heart infusion agar | 37° C., 18 hours, aerobic |
| Pseudomonas maltophilia | IFO 12690 | Heart infusion agar | 37° C., 18 hours, aerobic |
| Salmonella choleraesuis subsp. *choleraesuis* serovar *enteritidis* | JCM 1652 | Heart infusion agar | 37° C., 18 hours, aerobic |
| Salmonella choleraesuis subsp. *choleraesuis* serovar *thyphimutium* | JCM 6977 | Heart infusion agar | 37° C., 18 hours, aerobic |
| Serratia marcescens | ATCC 13880 | Heart infusion agar | 37° C., 18 hours, aerobic |
| Staphylococcus aureus | JCM 2151 | Heart infusion agar | 37° C., 18 hours, aerobic |
| Staphylococcus aureus | JCM 2179 | Heart infusion agar | 37° C., 18 hours, aerobic |
| Staphylococcus epidermidis | JCM 2414$^T$ | Heart infusion agar | 37° C., 18 hours, aerobic |
| Staphylococcus haemolyticus | ATCC29970 | Heart infusion agar | 37° C., 18 hours, aerobic |
| Staphylococcus hominis | ATCC27844 | Heart infusion agar | 37° C., 18 hours, aerobic |
| Staphylococcus hyicus | ATCC11249 | Heart infusion agar | 37° C., 18 hours, aerobic |
| Staphylococcus warneri | ATCC27836 | Heart infusion agar | 37° C., 18 hours, aerobic |

TABLE 4

| Strain | Strain No. | Medium | Conditions |
|---|---|---|---|
| Enterococcus avium | JCM8722 | Trypticase soy agarII with 5% sheep blood | 37° C., 18 hours, aerobic |
| Enterococcus casseliflavus | JCM 5675 | Trypticase soy agarII with 5% sheep blood | 37° C., 18 hours, aerobic |
| Enterococcus casseliflavus | JCM 5675 | Trypticase soy agarII with 5% sheep blood | 37° C., 18 hours, aerobic |
| Enterococcus casseliflavus | JCM 5675 | Trypticase soy agarII with 5% sheep blood | 37° C., 18 hours, aerobic |
| Enterococcus durans | JCM8725 | Trypticase soy agarII with 5% sheep blood | 37° C., 18 hours, aerobic |
| Enterococcus facalis | ATCC51299 | Trypticase soy agarII with 5% sheep blood | 37° C., 18 hours, aerobic |
| Enterococcus faecalis | JCM 5803 | Trypticase soy agarII with 5% sheep blood | 37° C., 18 hours, aerobic |
| Enterococcus faecium | JCM 5804 | Trypticase soy agarII with 5% sheep blood | 37° C., 18 hours, aerobic |
| Enterococcus gallinarum | JCM8728 | Trypticase soy agarII with 5% sheep blood | 37° C., 18 hours, aerobic |

TABLE 4-continued

| Strain | Strain No. | Medium | Conditions |
| --- | --- | --- | --- |
| *Enterococcus mundtii* | JCM8731 | Trypticase soy agarII with 5% sheep blood | 37° C., 18 hours, aerobic |
| *Streptococcus agalactiae* | ATCC13813 | Trypticase soy agarII with 5% sheep blood | 37° C., 18 hours, aerobic |
| *Streptococcus anginosus* | | Trypticase soy agarII with 5% sheep blood | 37° C., 18 hours, aerobic |
| *Streptococcus bovis* | JCM5802$^T$ | Trypticase soy agarII with 5% sheep blood | 37° C., 18 hours, aerobic |
| *Streptococcus constellatus* | | Trypticase soy agarII with 5% sheep blood | 37° C., 18 hours, aerobic |
| *Streptococcus dysgalactiae* | JCM5673 | Trypticase soy agarII with 5% sheep blood | 37° C., 18 hours, aerobic |
| *Streptococcus equinus* | JCM7879$^T$ | Trypticase soy agarII with 5% sheep blood | 37° C., 18 hours, aerobic |
| *Streptococcus milleri* | | Trypticase soy agarII with 5% sheep blood | 37° C., 18 hours, aerobic |
| *Streptococcus mitis* | | Trypticase soy agarII with 5% sheep blood | 37° C., 18 hours, aerobic |
| *Streptococcus mutans* | JCM5705$^T$ | Trypticase soy agarII with 5% sheep blood | 37° C., 18 hours, aerobic |
| *Streptococcus oralis* | | Trypticase soy agarII with 5% sheep blood | 37° C., 18 hours, aerobic |
| *Streptococcus pneumoniae* | | Trypticase soy agarII with 5% sheep blood | 37° C., 18 hours, aerobic |
| *Streptococcus pyogenes* | ATCC 10389 | Trypticase soy agarII with 5% sheep blood | 37° C., 18 hours, aerobic |
| *Streptococcus salivaris* subsp. *salivarius* | JCM5707$^T$ | Trypticase soy agarII with 5% sheep blood | 37° C., 18 hours, aerobic |
| *Streptococcus sanguis* | JCM5708$^T$ | Trypticase soy agarII with 5% sheep blood | 37° C., 18 hours, aerobic |
| *Streptococcus uberis* | JCM5709$^T$ | Trypticase soy agarII with 5% sheep blood | 37° C., 18 hours, aerobic |

TABLE 5

| Strain | Strain No. | Medium | Conditions |
| --- | --- | --- | --- |
| *Haemophilus aphrophirus* | cultiloops | Chocolate agar | 37° C., 18 hours, 5% $CO_2$ |
| *Haemophilus haemolyticus* | T-30 | Chocolate agar | 37° C., 18 hours, 5% $CO_2$ |
| *Haemophilus influenzae* | ATCC33391 | Chocolate agar | 37° C., 18 hours, 5% $CO_2$ |
| *Haemophilus parahaemolyticus* | T-13 | Chocolate agar | 37° C., 18 hours, 5% $CO_2$ |
| *Haemophilus parainfluenzae* | T-10 | Chocolate agar | 37° C., 18 hours, 5% $CO_2$ |
| *Neisseria gonorrhoeae* | ATCC49981 | Chocolate agar | 37° C., 18 hours, 5% $CO_2$ |
| *Neisseria meningitidis* Seroguroup B | | Chocolate agar | 37° C., 18 hours, 5% $CO_2$ |
| *Lactococcus garvieae* | JCM10343 | Modified GAM agar | 37° C., 24 hours, anaerobic |
| *Lactococcus lactis* subsp. *Lactis* | JCM5805 | Modified GAM agar | 37° C., 24 hours, anaerobic |
| *Lactococcus raffinolactis* | JCM5706 | Modified GAM agar | 37° C., 24 hours, anaerobic |
| *Leuconostoc mesenteroides* subsp. *dextranicum* | JCM9700 | Modified GAM agar | 37° C., 24 hours, anaerobic |
| *Leuconostoc mesenteroides* subsp. *mesenteroides* | JCM6124 | Modified GAM agar | 37° C., 24 hours, anaerobic |
| *Listeria monocytogenes* | 4b | Modified GAM agar | 37° C., 24 hours, anaerobic |
| *Pediococcus acidilactici* | JCM8797 | Modified GAM agar | 37° C., 24 hours, anaerobic |
| *Pediococcus damnosus* | JCM5886 | Modified GAM agar | 37° C., 24 hours, anaerobic |
| *Pediococcus pentosaceus* | JCM5890 | Modified GAM agar | 37° C., 24 hours, anaerobic |
| *Peptostreptococcus micros* | ATCC33270 | Modified GAM agar | 37° C., 24 hours, anaerobic |
| *Porphyromonas gingivalis* | | Modified GAM agar | 37° C., 24 hours, anaerobic |
| *Prevotella intermedia* | NCTC9336 | Modified GAM agar | 37° C., 24 hours, anaerobic |
| *Prevotella oris* | ATCC33573 | Modified GAM agar | 37° C., 24 hours, anaerobic |
| *Flavobacterium meningosepticum* | KM 506 | Modified GAM agar | 37° C., 24 hours, anaerobic |
| *Fusobacterium nucleatum* sbsp. *Nucleatum* | | Modified GAM agar | 37° C., 24 hours, anaerobic |
| *Acinetobacter baumannii* | ATCC23055 | Modified GAM agar | 37° C., 24 hours, anaerobic |
| *Actinomyces maeslundii* | ATCC19039 | Modified GAM agar | 37° C., 24 hours, anaerobic |
| *Corynebacterium matruchotii* | ATCC14266 | Modified GAM agar | 37° C., 24 hours, anaerobic |

TABLE 6

| Strain | Strain No. | Medium | Conditions |
| --- | --- | --- | --- |
| *Campylobacter jejuni* | | Skirrows medium | 37° C., 48 hours, microaerobic |
| *Campylobacter coli* | | Skirrows medium | 37° C., 48 hours, microaerobic |
| *Candida albicans* serotype A | A207 | Sabouraud-dextrose agar | 25° C., 48 hours, aerobic |
| *Candida albicans* serotype B | B792 | Sabouraud-dextrose agar | 25° C., 48 hours, aerobic |
| *Candida dubliniensis* | | Sabouraud-dextrose agar | 25° C., 48 hours, aerobic |
| *Candida glabrata* | | Sabouraud-dextrose agar | 25° C., 48 hours, aerobic |
| *Candida stellatoidea* | | Sabouraud-dextrose agar | 25° C., 48 hours, aerobic |
| *Candida parapsilosis* | | Sabouraud-dextrose agar | 25° C., 48 hours, aerobic |
| *Candida guilliermondii* | | Sabouraud-dextrose agar | 25° C., 48 hours, aerobic |
| *Candida kefyr* | | Sabouraud-dextrose agar | 25° C., 48 hours, aerobic |
| *Candida tropicalis* | | Sabouraud-dextrose agar | 25° C., 48 hours, aerobic |
| *Candidakrusei* | | Sabouraud-dextrose agar | 25° C., 48 hours, aerobic |
| *Cryptococcus neoformans* | ATCC24064 | Sabouraud-dextrose agar | 25° C., 48 hours, aerobic |

(2) Examination of Sensitivity and Cross-Reactivity by ELISA Method
(2-1) Construction of ELISA Method
(2-1-1) Method for Preparation of Immobilized Antibody and Method for Immobilization Ascites fluid containing monoclonal antibody MCM19 was applied to ammonium sulfate fractionation, IgG was purified using rProteinA Sepharose FF (GE healthcare), and a quantitative analysis of protein was carried out by a BCA method. The purified IgG antibody (10 μg/mL) was immobilized on a 96-well microplate.

(2-1-2) Method for Preparation of Antibody for Labeling with Alkaline Phosphatase and Method for Preparation of Labeled Antibody Ascites fluid containing monoclonal antibody MCM12 was applied to ammonium sulfate fractionation, and IgG was purified using MEP Hypercel (Pall Corporation). The IgG was digested with pepsin to prepare F(ab')$_2$, and F(ab')$_2$ was crosslinked with alkaline phosphatase to prepare an alkaline-phosphatase-labeled antibody.

(2-1-3) Method for Carrying Out ELISA Method

The immobilized 96-well microplate was washed, and blocked with 0.1 mmol/L TBS (pH 7.5) containing 1% BSA at room temperature for 1 hour. Each strain suspension to be tested (100 μL) was added to the microplate, and incubated at room temperature for 1 hour. The microplate was washed, and the alkaline-phosphatase-labeled antibody (10 μg/mL) was added and incubated at room temperature for 1 hour. The microplate was washed, and development was carried out using a substrate (pNPP) solution for 30 minutes. The reaction was stopped, and an absorbance at 405 nm was measured.

(3) Sensitivity Test

Test strains (1-1) were applied to the ELISA described above, and a test dilution which showed an absorbance of 0.05 or higher and a maximum dilution magnification was used to calculate the number of each strain. The results are shown in Table 7.

It was found from the results shown in Table 7 that the sensitivity against *Mycoplasma pneumoniae* was $10^3$ to $10^4$ cfu/mL by the ELISA using the monoclonal antibodies.

TABLE 7

| Strain | ATCC No. | Number of strain showing absorbance of 0.05 or higher (OD) by ELISA |
| --- | --- | --- |
| *Mycoplasma pneumoniae* FH | 15531 | $3.1 \times 10^4$ |
| *Mycoplasma pneumoniae* Bru | 15377 | $9.8 \times 10^4$ |
| *Mycoplasma pneumoniae* Mutant 22 | 39505 | $8.0 \times 10^4$ |
| *Mycoplasma pneumoniae* Mac | 15492 | $2.5 \times 10^4$ |
| *Mycoplasma pneumoniae* M52 | 15293 | $2.5 \times 10^3$ |
| *Mycoplasma pneumoniae* PI1428 | 29085 | $3.5 \times 10^3$ |
| *Mycoplasma pneumoniae* M129-B7 | 29342 | $3.8 \times 10^4$ |
| *Mycoplasma pneumoniae* UTMB-10P | 49894 | $2.3 \times 10^3$ |

(4) Cross-Reactivity Test

Test strains (1-2)[the genus *Mycoplasma* other than *Mycoplasma pneumoniae*, the genus *Ureaplasma*, and the genus *Acholeplasma* shown in Table 2] and test strains (1-3) [other bacteria and fungi shown in Table 3 to Table 6] were applied to the ELISA described above.

All the microorganisms other than *Mycoplasma genitalium* showed an absorbance of less than 0.010. With respect to *Mycoplasma genitalium*, the number thereof calculated from a test dilution which showed an absorbance of 0.05 or higher and a maximum dilution magnification was $6.9 \times 10^4$ cfu/mL.

As shown in these results, it was found that the ELISA using the monoclonal antibodies showed a cross-reactivity to *Mycoplasma genitalium*, but did not show a cross-reactivity to other microorganisms.

As described above, it was confirmed that the ELISA did not show a cross-reactivity to many bacteria and fungi which might disturb the diagnosis of a *Mycoplasma pneumoniae* or *Mycoplasma genitalium* infection.

Example 3

Examination of Sensitivity and Cross-Reactivity of Obtained Antibodies by Immunochromatography (1) Construction of Immunochromatography
(1-1) Preparation of Anti-Mycoplasma-Pneumoniae Antibody-Conjugated Colloidal Gold To a colloidal gold solution, of which pH was previously adjusted by adding 2 mL of a 50 mmol/L phosphate buffer (pH 11) to 18 mL of a colloidal gold solution (Tanaka Kikinzoku) having a diameter of 40 nm, 2.5 mL of 100 μg/mL monoclonal antibody MCM12 solution was added and stirred. After the mixture was stirred for 1 hour, 1 mL of 1 mass % polyethylene glycol (Mw. 20000, Wako Pure Chemical Industries) aqueous solution was added and stirred, and 2 mL of 10 mass % BSA aqueous solution (SIGMA) was added and stirred. This solution was centrifuged at 4° C. and 8000G for 15 minutes, and almost all the supernatant was removed so that approximately 1 mL of the supernatant was left. Colloidal gold was re-dispersed using an ultrasonic generator. The dispersed colloidal gold was dispersed into 20 mL of a phosphate buffer containing BSA, and centrifuged at 4° C. and 8000 G for 15 minutes. Almost all the supernatant was removed so that approximately 1 mL of the supernatant was left, and colloidal gold was re-dispersed using an ultrasonic generator to prepare an antibody-conjugated colloidal gold solution.

(1-2) Preparation of Pad Carrying Colloidal Gold

The antibody-conjugated colloidal gold solution prepared in (1-1) was diluted with the phosphate buffer containing BSA, and impregnated into a glass fiber pad (Millipore) which was previously cut to a size of 20 mm×300 mm. The pad was dried at room temperature overnight to prepare a pad carrying the colloidal gold antibody.

(1-3) Preparation of Antibody-Immobilized Membrane (Carrier for Chromatography)

Onto a nitrocellulose membrane (Millipore) which was cut to a size of 30 mm×300 mm, an antibody was immobilized in accordance with the following method to prepare an antibody-immobilized membrane. A solution of monoclonal antibody MCM19 for immobilization (5 mg/mL) was applied in a line with a width of approximately 1 mm, using a coater (BioDot), at a position 16 mm from one of the long sides of the membrane as the bottom, and dried to prepare the antibody-immobilized membrane.

(1-4) Construction of Kit for Immunochromatography

The antibody-immobilized membrane, the pad carrying colloidal gold, and an absorbent pad (Pall corporation) were attached to an adhesive back sheet so that adjacent pieces overlapped with each other. The resulting overlapped structure was cut along the long side with a width of 6 mm, using a cutter, to prepare test strips for immunochromatography. Each test strip was put into a housing case to prepare test kits for immunochromatography.

(1-5) Test Method

Cultivated strains, PBS-washed strains, culture supernatants, and pellets of cultivated strains were dissolved with a phosphate buffer containing Triton X-100 to prepare *Mycoplasma pneumoniae* antigen (or strain) solutions for test at predetermined concentrations. To each immunochromatographic kit for test, 100 µL of *Mycoplasma pneumoniae* antigen (or strain) solution for test was added dropwise. After 15 minutes from the addition, cases where a development was detected by the naked eye at the position on which the anti-Mycoplasma-pneumoniae antibody was coated of each antibody-immobilized membrane were judged as "positive", and cases where no development was detected were judged as "negative".

(2) Sensitivity Test

Test strains (1-1) in Example 2 were applied to the immunochromatography described above, and a test dilution which showed a development generated on the test line and a maximum dilution magnification was used to calculate the number of each strain. The results are shown in Table 8.

TABLE 8

| Strain | ATCC No. | Number of strain showing development by immunochromatography |
|---|---|---|
| *Mycoplasma pneumoniae* FH | 15531 | $3.1 \times 10^4$ |
| *Mycoplasma pneumoniae* Bru | 15377 | $9.8 \times 10^4$ |
| *Mycoplasma pneumoniae* Mutant 22 | 39505 | $8.0 \times 10^4$ |
| *Mycoplasma pneumoniae* Mac | 15492 | $2.5 \times 10^4$ |
| *Mycoplasma pneumoniae* M52 | 15293 | $2.5 \times 10^3$ |
| *Mycoplasma pneumoniae* PI1428 | 29085 | $3.5 \times 10^3$ |
| *Mycoplasma pneumoniae* M129-B7 | 29342 | $3.8 \times 10^4$ |
| *Mycoplasma pneumoniae* UTMB-10P | 49894 | $2.3 \times 10^3$ |

It was found from the results shown in Table 8 that the sensitivity against *Mycoplasma pneumoniae* was $10^3$ to $10^4$ cfu/mL by immunochromatography using the monoclonal antibodies.

(3) Cross-Reactivity Test

Test strains (1-2)[the genus *Mycoplasma* other than *Mycoplasma pneumoniae*, the genus *Ureaplasma*, and the genus *Acholeplasma* shown in Table 2] and test strains (1-3) [other bacteria and fungi shown in Table 3 to Table 6] of Example 2 were applied to the immunochromatography described above.

All the microorganisms other than *Mycoplasma genitalium* were negative, i.e., did not show any developments. By contrast, a development was detected in *Mycoplasma genitalium*, and the number thereof calculated from a test dilution showing a maximum dilution magnification was $6.9 \times 10^4$ cfu/mL.

As shown in these results, it was found that the immunochromatography using the monoclonal antibodies showed cross-reactivity to *Mycoplasma genitalium*, but did not show a cross-reactivity to other microorganisms.

As described above, it was confirmed that the immunochromatography did not show cross-reactivity to many bacteria and fungi which might disturb the diagnosis for a *Mycoplasma pneumoniae* or *Mycoplasma genitalium* infection.

Example 4

Evaluation of Clinical Specimens

Pharyngeal swabs were collected from 3 patients suspected of suffering with a mycoplasma infection and 33 healthy persons, and a detection of *Mycoplasma pneumoniae* was carried out in accordance with the immunochromatography of Example 3. As a result, a positive reaction was observed in the 3 patients suspected of suffering with a mycoplasma infection, and the 33 healthy persons were negative, as shown in Table 9.

DNAs were extracted from the same samples in accordance with a conventional method, and a gene detection of *Mycoplasma pneumoniae* was carried out using a modified method derived from the qualitative PCR method of Jensen et al. (APMIS. 1989; 97(11): 1046-8.), in which part of a *Mycoplasma pneumoniae* P1 gene (*M. pneumoniae* M129-B7 NCBI number: NC_000912) was amplified, and both were compared to each other. Both positive and negative results accorded with each other, as shown in Table 9.

TABLE 9

|  |  | Immunochromatography | | |
|---|---|---|---|---|
|  |  | Positive | Negative | Total |
| PCR | Positive | 3 | 0 | 3 |
|  | Negative | 0 | 33 | 33 |
| Total |  | 3 | 33 | 36 |

Positive agreement rate: 100% (3/3)
Negative agreement rate: 100% (33/33)
Overall agreement rate: 100% (36/36)

Next, DNAs derived from the samples which showed positive by both the immunochromatography and the qualitative PCR method was used, and a gene detection of *Mycoplasma genitalium* was carried out using a modified method derived from the qualitative PCR method of Yoshida et al. (J Clin Microbiol. 2002; 40(4): 1451-5.) for *Mycoplasma genitalium*, in which part of a *Mycoplasma genitalium* 16s rRNA region (*M. genitalium* G7 NCBI number: L43967) was amplified. As a result, the gene derived from *Mycoplasma genitalium* was not detected in any of the samples, as shown in Table 10.

In this manner, it was confirmed that the gene derived from *Mycoplasma genitalium* could be amplified by this method.

TABLE 10

| Clinical specimen | *M. genitalium* PCR |
|---|---|
| Sample A | — |
| Sample B | — |
| Sample C | — |

As described above, it was shown that the antibody of the present invention was used to specifically detect *Mycoplasma pneumoniae*, and a mycoplasma infection can be diagnosed.

Example 5

Amplification of DnaK gene of *Mycoplasma pneumoniae* Culture Strains

As samples to be measured, 8 strains of *Mycoplasma pneumoniae* purchased from ATCC (*M. pneumoniae* FH: ATCC No. 15531, *M. pneumoniae* Bru: ATCC No. 15377, *M. pneumoniae* Mac: ATCC No. 15492, *M. pneumoniae* Mutant 22: ATCC No. 39505, *M. pneumoniae* M52: ATCC No. 15293, *M. pneumoniae* PI1428: ATCC No. 29085, *M. pneumoniae* M129-B7: ATCC No. 29342, and *M. pneumoniae* UTMB-10P: ATCC No. 49894) were used. These 8 strains of *Mycoplasma pneumoniae* were cultivated in a PPLO medium, and DNAs were extracted.

The DNA extraction was carried out using a Sumitest EX-R&D kit (Medical & Biological Laboratories), and each DNA was suspended in 10 mmol/L Tris-HCl, 1 mmol/L EDTA Buffer pH 8.0 (Nippon Gene)(hereinafter referred to as TE Buffer) and cryopreserved at −40° C.

With respect to the extracted DNAs, the number of gene copies was determined by a mycoplasma common quantitative PCR for 16s rRNA region. Each DNA was diluted with TE buffer to prepare 10-fold diluted preparations from $2\times10^6$ to $2\times10^0$ copies/µL. These were used in detecting the DnaK gene.

The mycoplasma common quantitative PCR for 16s rRNA region was carried out as follows.

Primers which were common to the genus *Mycoplasma* for amplifying the 16s rRNA region were designed, and the number of gene copies in each extracted *M. pneumoniae* DNA was calculated by a real-time PCR method using a standard. The real-time PCR was carried out using LightCycler FastStart DNA Master SYBR Green I (Roche Applied Science).

The following primer sequences were used. *M. pneumoniae* M129-B7 complete genome: GenBank Accession No. NC_000912

(SEQ ID NO: 2)
FmY4: 5'-TGGGGAGCAAA(C/T)AGGATTAG-3'
nt 119,081-119,100 20 mer (SEQ ID NO: 3)
MGSO-2: 5'-CACCATCTGTCACTCTGTTAACCTC-3'
nt 119,332-119,356 25 mer With regard to the PCR conditions, a reaction at 95° C. for 10 minutes was carried out and a cycle composed of reactions at 94° C. for 10 seconds for denaturing, at 60° C. for 2 seconds for annealing, and at 72° C. for 12 seconds was repeated 50 times.

As the standard, a diluted series ($10^7$, $10^5$, $10^3$, $10^2$, and $10^1$ copies/test) of pT7Blue T-Vector (Takara Bio) in which part of 16s rRNA (771 bp: 302-1072 for 16s rRNA) of *M. pneumoniae* (M129 strain) was recombined was used. The number of copies in the standard was calculated on the basis of the following equations:

$$DNA \text{ concentration (µg/mL)} = ABS(260 \text{ nm}) \times 50$$
$$1 \text{ pmol of kbp } DNA = 0.66 \text{ µg}$$

$$\text{copy(copies/mL)} = \frac{1}{0.66} \times \left\{ \frac{1000 \text{ bp}}{Lp+Lr} \times (A260 \times 50) \times (6.02 \times 10^{23}) \right\} \times 10^{-12} \quad [\text{Math. 1}]$$

Lp: Length of plasmid
Lr: Length of recombinant DNA

Next, the DnaK gene of *Mycoplasma pneumoniae* was amplified by PCR as follows. With regard to a PCR reaction liquid, 25 µL of Premix EX Taq Hot Start Version (TaKaRa), 1 µL of 10 pmol/µL sense primer MpDnaK_S, and 1 µL of 10 pmol/µL antisense primer MpDnaK_A were added to 18 µL of Otsuka distilled water (Otsuka Pharmaceutical) to prepare 45 µL of a master mixture, and 5 µL of each extracted DNA was added to the master mixture to adjust the total volume to 50 µL. TE buffer was used as a PCR negative control. To amplify the DnaK gene having a complete length of 1,788 bp, the sense primer was designed at 81 bp 5'-upstream from the starting codon of the DnaK gene, and the antisense primer was designed at 53 bp 3'-downstream from the stop codon. More particularly, sense primer MpDnaK_S corresponded to the 521,756-521,782 nucleotide sequence of *M. peumoniae* M129 (GenBank Acc No. NC_000912), and antisense primer MpDnaK_A corresponded to the 523,655-523,677 nucleotide sequence.

(SEQ ID NO: 4)
MpDnaK_S: 5'-CTCAAACGCTAAAAGTGCTAACG-3' 23 mer (SEQ ID NO: 5)
MpDnaK_A: 5'-AAACCATTATTACAGGTCAAATAAGAC-3' 27 mer In the PCR reaction, using a Mastercycler (Eppendorf), a cycle composed of reactions at 94° C. for 30 seconds for denaturing, at 50° C. for 30 seconds for annealing, and at 72° C. for 2 minutes was repeated 50 times, and finally a reaction at 72° C. for 5 minutes was carried out. After the PCR reaction, 5 µL of each PCR product was subjected to 2% agarose electrophoresis, and the agarose gel was stained with ethidium bromide and irradiated with ultraviolet light to confirm an amplified band of approximately 1,900 bp.

The 8 *Mycoplasma pneumoniae* stains prepared above were examined to confirm that all the 8 strains could be amplified up to $10^2$ copies/test.

Example 6

Cross-Reactivity to *Mycoplasma* Culture Strains Isolated from Human

As samples to be measured, 17 *mycoplasma* strains purchased from ATCC (*M. genitalium*: ATCC No. 33530, *M. hominis*: ATCC No. 23114, *Ureaplasma parvum*: ATCC No. 700970, *U. urealyticum*: ATCC No. 27618, *M. fermentans*: ATCC No. 19989, *Acholeplasma laidlawii*: ATCC No. 23206, *A. oculi*: ATCC No. 51735, *M. penetrans*: ATCC No. 55252, *M. pirum*: ATCC No. 25960, *M. orale*: ATCC No. 23714, *M. salivarium*: ATCC No. 23064, *M. arthritidis*: ATCC No. 19611, *M. buccale*: ATCC No. 23636, *M. faucium*: ATCC No. 25293, *M. lipophilum*: ATCC No. 27104, *M. primatum*: ATCC No. 25948, and *M. spermatophilum*: ATCC No. 49695) were used. These 17 mycoplasma strains were cultivated in a PPLO medium. Similar to Example 5, DNAs were extracted, the number of gene copies was determined by the quantitative PCR for 16s rRNA region, and each DNA was diluted to $2\times10^5$ copies/µL.

The procedures described in Example 5 were repeated, except that the 17 *Mycoplasma* strains were used as the samples to be measured, to carry out the PCR for the DnaK gene of *Mycoplasma pneumoniae*, and no amplified band was detected in any of the 17 strains. Because no cross-reactivity was detected when the concentration of the DNA sample was 10,000 times that of DNA capable of amplifying the DnaK gene of *M. pneumoniae*, it was found that the PCR for the DnaK gene of *Mycoplasma pneumoniae* had an extremely high specificity.

Example 7

Amplification of DnaK Gene of *Mycoplasma pneumoniae* from Clinical Specimens

As samples to be measured, extracted DNAs from 46 cases of positive clinical specimens (40 cases of pharyngeal swabs, 2 cases of nasal mucus, 1 case of nasopharyngeal aspirates, and 3 cases of nasopharyngeal swabs) and 30 cases of negative specimens (10 cases of pharyngeal swabs from healthy persons, 10 cases of pharyngeal swab from clinical specimens, 4 cases of nasal mucus, 3 cases of nasopharyngeal aspirates, and 3 cases of nasopharyngeal swabs) were tested by a nested PCR for the *Mycoplasma pneumoniae* P1 gene region, described in the "*Mycoplasma pneumonia*" section of National Institute of Infectious Diseases, "Pathogen Detection Manual" p. 1309-1344.

The PCR for the DnaK gene of *Mycoplasma pneumoniae* was carried out to confirm that the DnaK gene was amplified in all 46 cases of P1 gene PCR positive. By contrast, the DnaK gene was not amplified in any of the 30 cases of P1 gene PCR negative.

TABLE 11

|  |  | DnaK gene PCR | | |
|---|---|---|---|---|
|  |  | Positive | Negative | Total |
| P1 gene PCR | Positive | 46 | 0 | 46 |
|  | Negative | 0 | 30 | 30 |
| Total |  | 46 | 30 | 76 |

Example 8

Analysis of DnaK Gene Nucleotide Sequence from Culture Strains and Clinical Specimens The nucleotide sequences of PCR products from the 8 ATCC strains of Example 5 and the 8 clinical specimens (7 cases of pharyngeal swabs and 1 case of nasopharyngeal swabs) of Example 7, in which the amplification was detected by the PCR for DnaK gene, were determined using a BigDye Terminator v3.1 (Applied Biosystems) and a 3130×1 Genetic Analyzer (Applied Biosystems).

As a result, with respect to the DnaK gene (1,788 bp, SEQ ID NO: 6), the PCR products from the 8 ATCC strains and the 8 clinical specimens absolutely (100%) accorded with each other, and also absolutely (100%) accorded with the M129 strain (Acc No. NC_000912) and FH strain (Acc No. CP002077) registered in GenBank. The alignment between the M129 stain and the FH strain is shown in FIGS. 1 to 3.

With respect to the P1 gene, differential typing was carried out by a PCR-RLFP method in accordance with the reference: JOURNAL OF CLINICAL MICROBIOLOGY, 1996, p. 447-449 Vol. 34, No. 2, and the 8 ATTC strains of Example 5 were classified into two groups. More particularly, 4 strains including M129-B7, M52, PI1428, and Mutant 22 were classified into Type I, and 4 strains including FH, Bru, Mac, and UTMB-10P were classified into Type II. The alignment between the M129 strain (SEQ ID NO: 7) and the FH strain (SEQ ID NO: 8) as typical strains is shown in FIGS. 4 to 10.

It was considered from these results that the obtained antibodies show no difference in reactivity with respect to the genotype, the place for collection, and the time of collection, because the DnaK genes absolutely (100%) accorded with each other, even among strains in which the types of the P1 gene were different, and no variations in the nucleotide sequence were detected among strains collected from various places and over the past 50 years.

INDUSTRIAL APPLICABILITY

According to the present invention, *Mycoplasma pneumoniae* and/or *Mycoplasma genitalium* can be specifically detected with high sensitivity in specimens such as oral swab specimens, nasal cavity swab specimens, urine, tissue samples, or body fluids, or samples derived from culture. In particular, the present invention is important for the diagnosis of atypical pneumonia caused by *Mycoplasma pneumoniae* or the diagnosis of nongonococcal urethritis and sexually transmitted disease caused by *Mycoplasma genitalium*, and is industrially applicable to the manufacture of pharmaceuticals.

Although the present invention has been described with reference to specific embodiments, various changes and modifications obvious to those skilled in the art are possible without departing from the scope of the appended claims.

The invention claimed is:

1. An anti-DnaK monoclonal antibody specific to *Mycoplasma pneumoniae* and *Mycoplasma genitalium*.

2. A kit for diagnosing *Mycoplasma pneumoniae* or *Mycoplasma genitalium*, comprising the anti-DnaK monoclonal antibody according to claim 1.

* * * * *